(12) United States Patent
Collis et al.

(10) Patent No.: US 6,750,214 B2
(45) Date of Patent: Jun. 15, 2004

(54) QUINOLINE AND QUINAZOLINE COMPOUNDS USEFUL IN THERAPY

(76) Inventors: Alan John Collis, 235 E. 42nd St., New York, NY (US) 10017; David Nathan Abraham Fox, 235 E. 42nd St., New York, NY (US) 10017; Julie Newman, 235 E. 42nd St., New York, NY (US) 10017

( * ) Notice: Subject to any disclaimer, the term of this patent is extended or adjusted under 35 U.S.C. 154(b) by 47 days.

(21) Appl. No.: 10/455,546

(22) Filed: Jun. 4, 2003

(65) Prior Publication Data

US 2003/0220332 A1 Nov. 27, 2003

Related U.S. Application Data

(62) Division of application No. 09/812,083, filed on Mar. 19, 2001, now Pat. No. 6,642,242, which is a continuation of application No. 09/613,500, filed on Jul. 10, 2000, now abandoned, which is a division of application No. 09/091,370, filed as application No. PCT/EP96/05609 on Dec. 5, 1996, now Pat. No. 6,103,738.

(30) Foreign Application Priority Data

Dec. 23, 1995 (GB) .............................................. 9526546

(51) Int. Cl.⁷ .................... A01N 31/519; C07D 491/052
(52) U.S. Cl. ............... 514/217.06; 514/257; 514/228.5; 514/232.8; 514/252.16; 514/259.4; 514/218; 544/58.2; 544/115; 544/247; 540/575; 540/600
(58) Field of Search .......................... 514/217.06, 257, 514/228.5, 232.8, 252.16, 259.4, 218, 266.2, 266.21, 286.24; 544/58.2, 115, 247; 540/575, 600

(56) References Cited

U.S. PATENT DOCUMENTS 6,103,738 A * 8/2000 Collis et al. ................. 514/311
6,642,242 B2 * 11/2003 Collis et al. ................. 514/260

FOREIGN PATENT DOCUMENTS

EP 0100200 6/1987
GB 2171997 10/1986

OTHER PUBLICATIONS

Hieble J.P. et al., Journal of Medicinal Chemistry, vol. 38, No. 18, Sep. 1, 1995, "α–and β–Adrenoceptors: From the Gene to the Clinic. 1. Molecular Biology and Adrenoceptor Subclassification.".

* cited by examiner

Primary Examiner—John M Ford

(57) ABSTRACT

The invention provides compounds of formula (I),

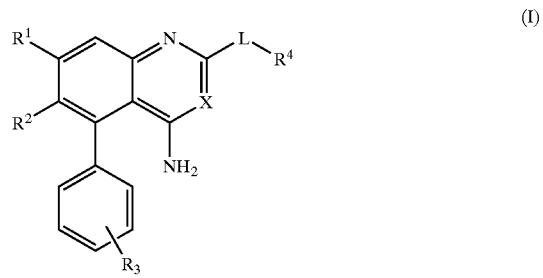

wherein $R^1$ represents $C_{1-4}$ alkoxy optionally substituted by one or more fluorine atoms; $R^2$ represents H or $C_{1-6}$ alkoxy optionally substituted by one or more fluorine atoms; $R^3$ represents one or more groups independently selected from H, halogen, $C_{1-4}$ alkoxy and $CF_3$; in addition, $R^2$ and one $R^3$ group may together represent $-OCH_2-$, the methylene group being attached to the ortho-position of the pendant phenyl ring; $R^4$ represents a 4-, 5- or 6-membered heterocyclic ring containing 1 or 2 heteroatoms selected from N, O and S, the ring being optionally fused to a benzene ring or a 5- or 6-membered heterocyclic ring containing 1 or 2 heteroatoms selected from N, O and S, the ring system as a whole being optionally substituted; X represents CH or N; and L is absent or represents a cyclic group or an open chain group; and the pharmaceutically acceptable salts thereof. The compounds of formula (I) are useful in the treatment of inter alia benign prostatic hyperplasia.

8 Claims, No Drawings

QUINOLINE AND QUINAZOLINE COMPOUNDS USEFUL IN THERAPY

This application is a divisional of U.S. Ser. No. 09/812,083, filed Mar. 19, 2001, now U.S. Pat. No. 6,642,242 which is a continuation of U.S. Ser. No. 09/613,500, filed Jul. 10, 2000, now abandoned, which is a division of U.S. Ser. No. 09/091,370, filed Jun. 17, 1998, now U.S. Pat. No. 6,103,738, which is a 35 U.S.C. §371 filing of PCT/EP96/05609, filed Dec. 5, 1996, which claims priority to GB Application No. 9526546.8, filed Dec. 23, 1995.

This invention relates to novel compounds useful in therapy, particularly in the treatment of benign prostatic hyperplasia.

International Patent Application WO 89/05297 discloses a number of substituted quinazoline compounds which are indicated as inhibitors of gastric acid secretion.

According to the present invention, there is provided a compound of formula I,

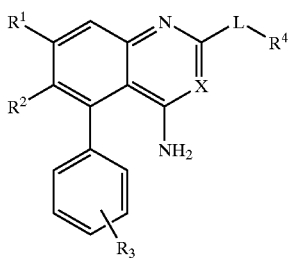

wherein
$R^1$ represents $C_{1-4}$ alkoxy optionally substituted by one or more fluorine atoms;
$R^2$ represents H or $C_{1-6}$ alkoxy optionally substituted by one or more fluorine atoms;
$R^3$ represents one or more groups independently selected from H, halogen, $C_{1-4}$ alkoxy and $CF_3$;
in addition, $R^2$ and one $R^3$ group may together represent —$OCH_2$—, the methylene group being attached to the ortho-position of the pendant phenyl ring;
$R^4$ represents a 4-, 5- or 6-membered heterocyclic ring containing 1 or 2 heteroatoms selected from N, O and S, the ring being optionally fused to a benzene ring or a 5- or 6-membered heterocyclic ring containing 1 or 2 heteroatoms selected from N, O and S, the ring system as a whole being optionally substituted by one or more groups independently selected from OH, $C_{1-4}$ alkyl, $C_{1-4}$ alkoxy, halogen, $SO_2NR^8R^9$ and $NHSO_2(C_{1-4}$ alkyl), and when S is a member of the ring system, it may be substituted by one or two oxygen atoms;
$R^8$ and $R^9$ independently represent H or $C_{1-4}$ alkyl;
X represents CH or N; and
L is absent,
or represents a cyclic group of formula Ia,

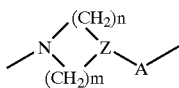

in which N is attached to the 2-position of the quinoline or quinazoline ring;
A is absent or represents CO or $SO_2$;
Z represents CH or N;
m represents 1 or 2, and in addition, when Z represents CH, it may represent 0; and
n represents 1, 2 or 3, provided that the sum of m and n is 2, 3, 4 or 5;
or represents a chain of formula Ib,

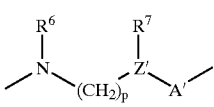

in which N is attached to the 2-position of the quinoline or quinazoline ring;
A' and Z' have the same significance as A and Z above, respectively;
$R^6$ and $R^7$ independently represent H or $C_{1-4}$ alkyl; and
p represents 1, 2 or 3, and in addition, when Z' represents CH, it may represent 0;
or a pharmaceutically acceptable salt thereof (referred to together herein as "the compounds of the invention").

Pharmaceutically acceptable salts include acid addition salts, such as hydrochloride and hydrobromide salts, and phosphate salts.

Alkyl and alkoxy groups that $R^{1-4}$ may represent or include can be straight chain, branched chain, cyclic, or a combination thereof Heterocyclic groups that $R^4$ represents may be saturated or unsaturated.

The compounds of the invention may be optically active. In particular, they may exhibit atropisomerism about the bond joining the pendant phenyl ring to the rest of the molecule when an $R^3$ substituent is in the 2- or 3-position of the phenyl ring. The invention includes all optical isomers of the compounds of formula I, and all diastereoisomers thereof.

Preferred groups of compounds that may be mentioned include those in which:

(a) $R^1$ represents methoxy;
(b) $R^2$ represents methoxy;
(c) $R^2$ and an $R^3$ group together represent —$OCH_2$—;
(d) $R^3$ represents H or 4-fluoro;
(e) $R^4$ represents a group having the formula II, III, IV, V or VI,

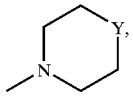

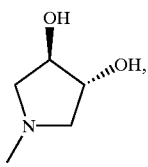

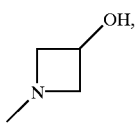

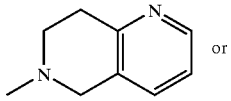

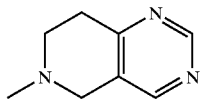

wherein

Y represents O, $CH_2$, $SO_2$, $NR^5$ or CHF; and $R^5$ represents H or $C_{1-4}$ alkyl;

the group of formula II being of particular interest, especially when Y represents O; and (f) L represents a group of formula VII,

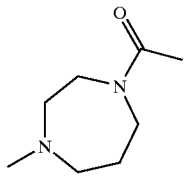

or is absent, this latter preference being of particular interest when $R^4$ represents a group of formula V or VI.

According to the invention, there is also provided a process for the production of a compound of the invention, which comprises:

(a) when X represents CH, cyclizing a compound of formula X,

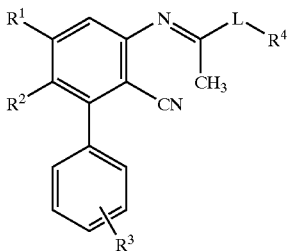

in which $R^{1-4}$ and L are as defined above;

(b) when A or A' is present, and Z or Z' represents N, reacting a compound of formula XIIIa or XIIIb, as appropriate,

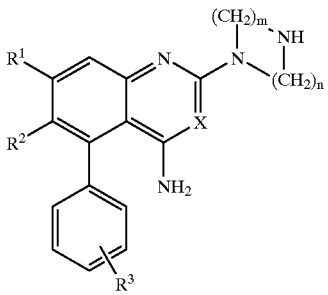

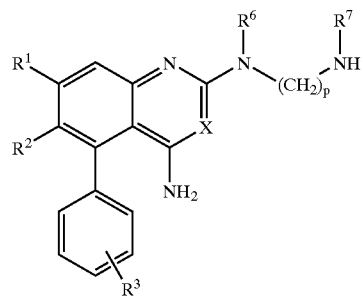

in which $R^{1-3}$, $R^6$, $R^7$, X, m, n and p are as defined above, with a compound of formula XIV,

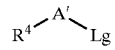

in which $R^4$ is as defined above, A' represents CO or $SO_2$ and Lg represents a leaving group;

(c) reacting a compound of formula XVIII,

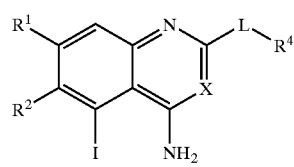

in which $R^1$, $R^2$, $R^4$, X and L are as defined above, with a compound of formula XIX,

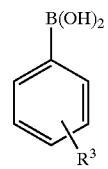

in which $R^3$ is as defined above; or (d) when X represents N, reacting a compound of formula XXII,

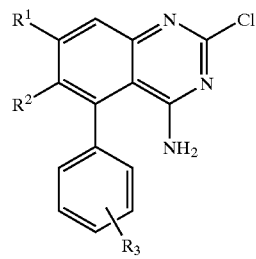

in which $R^{1-3}$ are as defined above, with a compound of formula XXIIIa or XXIIIb, as appropriate, XXIIIa $$\underset{HN}{(CH_2)_n} \underset{(CH_2)_m}{Z} A \underset{R^4}{}$$

XXIIIb $$\underset{H}{R^6} \underset{N}{N} \underset{(CH_2)_p}{\overset{R^7}{Z'}} A' R^4$$

in which $R^4$, $R^6$, $R^7$, A, A', Z, Z', m, n and p are as defined above;

(e) when A or A' represents CO, reacting a compound of formula XXVIIIa or XXVIIIb, as appropriate, XXVIIIa

[structure showing quinazoline with $R^1$, $R^2$, $NH_2$, X, phenyl-$R^3$, and $(CH_2)_m$-Z-N-$(CH_2)_n$ chain with C(O)-Lg]

XXVIIIb

[structure showing quinazoline with $R^1$, $R^2$, $NH_2$, X, phenyl-$R^3$, and $R^6$-N-$(CH_2)_p$-Z'-C(O)-Lg with $R^7$]

in which $R^{1-3}$, $R^6$, $R^7$, X, Z, Z', m, n and p are as defined above, and Lg is a leaving group, with a compound of formula XXIX, HR$^{4a}$    XXIX in which R$^{4a}$ represents the groups defined by $R^4$ above which contain a nucleophilic nitrogen atom in the ring, this nucleophilic nitrogen atom being attached to H;

(f) conversion of a compound of formula I in which L represents a cyclic group of formula Ia, to a corresponding compound of formula I in which L represents a chain of formula Ib in which $R^6$ and $R^7$ each represent H, by the action of a strong base;

(g) when A or A' is absent and Z or Z' represents N, reacting a compound of formula XIIIa or XIIIb, as defined above, with a compound of formula XXX, $R^4$-Hal    XXX in which $R^4$ is as defined above and Hal represents a halogen atom attached to the ring; or (h) when $R^2$ and one $R^3$ group together represent —OCH$_2$—, cyclization of a compound of formula XXXI,

XXXI

[structure showing quinazoline with $R^1$, $NH_2$, L-$R^4$, X, O-CH$_2$-phenyl with Br and $R_3$]

in which $R^1$, $R^4$, X and L are as defined above, and $R^{3a}$ has the same meaning as $R^3$ above except that $R^2$ and an $R^{3a}$ group do not together represent —OCH$_2$—;

a and where desired or necessary converting the resulting compound of the invention into a pharmaceutically acceptable salt or vice versa.

In process (a), the cyclization may be carried out in the presence of a strong base (for example lithium diisopropylamide) in a solvent which does not adversely affect the reaction (for example tetrahydrofuran) around room temperature and quenched with water.

In process (b), suitable leaving groups are OH and Cl. When the compound of formula XIV is a carboxylic acid, the reaction may be carried out in the presence of conventional coupling agents [for example 1-hydroxybenzotriazole monohydrate, 1-(3-dimethylaminopropyl)-3-ethylcarbodiimide hydrochloride and 4-methylmorpholine] in a solvent which does not adversely affect the reaction (for example CH$_2$Cl$_2$) at or around room temperature. When the leaving group is Cl. The reaction may be carried out in a solvent which does not adversely affect the reaction (for example CH$_2$Cl$_2$) around 0° C.

In process (c), the reaction may be carried out in the presence of a palladium catalyst [for example tetrakis(triphenylphosphine)palladium] in a solvent which does not adversely affect the reaction (for example a mixture of toluene, ethanol and 1N aqueous sodium carbonate) at an elevated temperature (for example the reflux temperature of the solvent).

In process (d), the reaction may be carried out in a solvent which does not adversely affect the reaction (for example n-butanol) in the presence of a base (for example triethylamine) at an elevated temperature (for example 100° C.).

In process (e), suitable leaving groups include Cl. The reaction may be carried out in a solvent which does not adversely affect the reaction (for example THF) in the presence of a base (for example triethylamine) at room temperature.

The reaction may also be carried out without isolating the compound of formula XXVIIIa or XXVIIIb, by reacting a compound of formula XIIIa or XIIIb with triphosgene and a compound of formula XXIX. In this case the leaving group is —Cl. The reaction may be carried out in a solvent which does not adversely affect the reaction (for example CH$_2$Cl$_2$) in the presence of a base (for example triethylamine) at or around room temperature.

In process (f), suitable strong bases include lithium diisopropylamide. The reaction may be carried out in a solvent which does not adversely affect the reaction (for example THF).

In process (g), the reaction may be carried out in a solvent which does not adversely affect the reaction (for example a mixture or n-BuOH and dimethylacetamide) in the presence of a base (for example triethylamine) at an elevated temperature (for example 80° C.).

In process (h), suitable reagents are sodium carbonate with palladium acetate. The reaction may be carried out in a solvent which does not adversely affect the reaction (for example dimethylacetamide) at an elevated temperature (for example 130° C.).

It will be apparent to those skilled in the art that in the processes described above [for example process (c)], and in the methods given below for preparation of the starting materials used in the above processes, when $R^2$ and $R^3$ are present in different molecules, they cannot together represent —$OCH_2$—.

Compounds of formula X [see process (a)] may be prepared by reaction of a compound of formula XI,

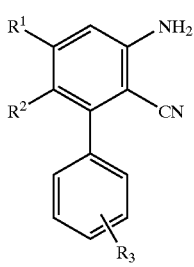

XI in which $R^{1-3}$ are as defined above, with a combination of a compound of formula XII,

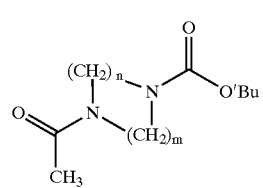

XII in which $R^4$ and L are as defined above, and phosphorous oxychloride in dichloromethane at the reflux temperature of the solvent.

Compounds of formula XIIIa or XIIIb [see process (b)] in which X represents CH may be prepared from compounds of formula XVa or XVb, as appropriate, XVa

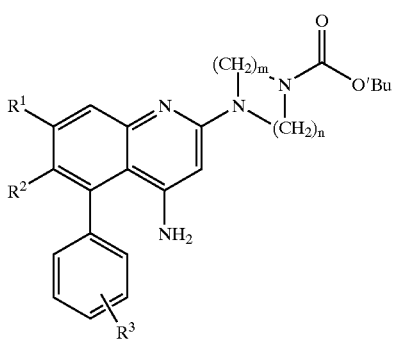

XVb

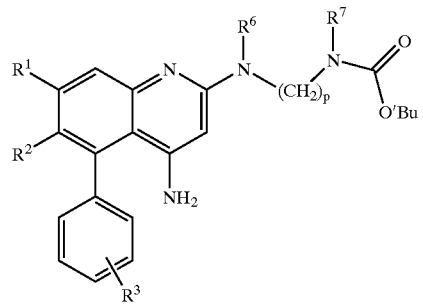

in which $R^{1-3}$, $R^6$, $R^7$, m, n and p are as defined above, by bubbling HCl gas through a solution of the compound in dichloromethane.

Compounds of formula XVa or XVb may be prepared from compounds of formula XVIa or XVIb, as appropriate, XVIa

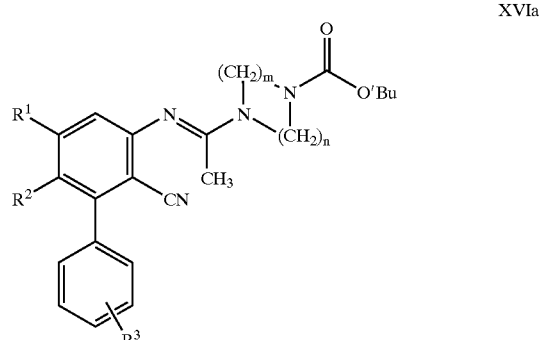

XVIb

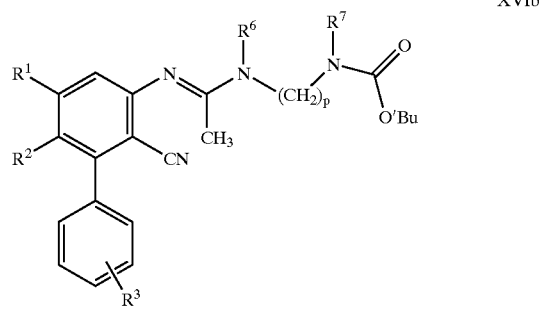

in which $R^{1-3}$, $R^6$, $R^7$, m, n and p are as defined above, by cyclization using potassium hydroxide or lithium diisopropylamide at an elevated temperature (such as 90° C.) in DMSO, quenching with water.

Compounds of formula XVIa or XVIb may be prepared by reacting a compound of formula XI, as defined above, with a compound of formula XVIIa or XVIIb, as appropriate, XVIIa

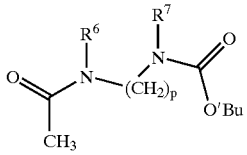
XVIIb in which R⁶, R⁷, m, n and p are as defined above, by the method described above for producing compounds of formula X.

Compounds of formula XIIIa or XIIIb in which X represents N may be prepared by reacting a compound of formula XXII,

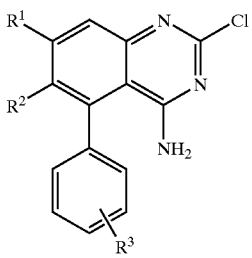
XXII in which R¹⁻³ are as defined above, with a compound of formula XXIIa or XXIIb, as appropriate,

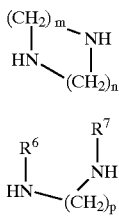
XXIIa

XXIIb in which R⁶, R⁷, m, n and p are as defined above, using the conditions mentioned for process (d) above.

Compounds of formula XVIII [see process (c)] in which X represents CH may be prepared by cyclization of a compound of formula XX,

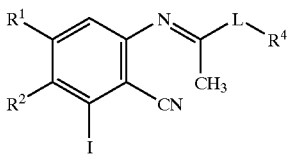
XX in which R¹, R², R⁴ and L are as defined above, using the reaction conditions mentioned in process (a) above.

Compounds of formula XX may be prepared by reacting a compound of formula XXI,

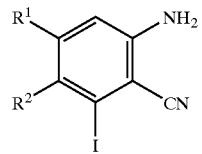
XXI in which R¹ and R² are as defined above, with a compound of formula XII as defined above, using the method described above for the preparation of compounds of formula X.

Compounds of formula XVIII in which X represents N may be prepared by reacting a compound of formula XXVII,

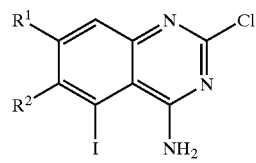
XXVII in which R¹ and R² are as defined above, with a compound of formula XXIIIa or XXIIIb, as appropriate, as defined above, using the reaction conditions mentioned above for process (d).

Compounds of formula XXII [see process (d)] may be prepared from a compound of formula XXIV,

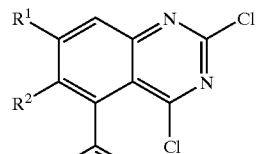
XXIV

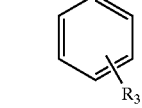

in which R¹⁻³ are as defined above, by reaction with a saturated solution of ammonia in methanol.

Compounds of formula XXIV may be prepared from a compound of formula XXV,

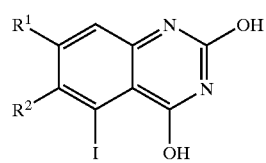
XXV in which R¹ and R² are as defined above, by reaction with a compound of formula XIX as defined above using the reaction conditions described above for process (c), followed by reaction with POCl₃ and N,N-dimethylaniline.

Compounds of formula XXV may be prepared from a compound of formula XXVI,

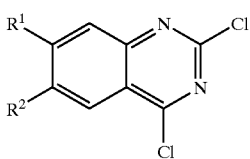

in which $R^1$ and $R^2$ are as defined above, using conventional techniques.

Compounds of formula XXVIIIa and XXVIIIb [see process (e)] in which Lg represents Cl may be prepared from compounds of formula XIIIa or XIIIb, as appropriate, by reaction with triphosgene. The reaction may be carried out in a solvent which does not adversely affect the reaction (for example $CH_2Cl_2$) in the presence of a base (for example triethylamine) at around $-10°$ C.

Compounds of formula XXXI [see process (h)] may be prepared from compounds of formula XXXII,

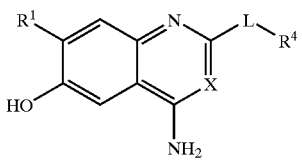

in which $R^1$, $R^4$, L and X are as defined above, by reaction with a compound of formula XXXIII,

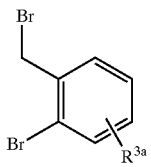

wherein $R^{3a}$ is as defined above, in the presence of sodium hydride in DMF at room temperature.

Compounds of formula XXXI are analogous to compounds of formula I, and may be prepared using analogous methods. For example, when X represents CH, the compounds may be prepared by cyclizing a compound analogous to those of formula X using process (a). When X represents N, the compounds may be prepared from a compound analogous to those of formula XXI and a compound of formula XXIIIa or XXIIIb, as appropriate, using process (d).

Compounds of formulae XI, XII, XIV, XVIIa, XVIIb, XIX, XXI, XXIIa, XXIIb, XXIII, XXVI, XXIX, XXX and XXXIII are either known or are available using known techniques.

The intermediate compounds of formulae X, XIIIa, XIIIb, XVIII, XXII, XXVIIIa, XXVIIIb and XXI form a further aspect of the invention.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991.

The compounds of the invention are useful because they possess pharmacological activity in animals. In particular, the compounds are useful in the treatment of a number of conditions including hypertension, myocardial infarction, male erectile dysfunction, hyperlipidaermia, cardiac arrhythmia and benign prostatic hyperplasia. The latter condition is of greatest interest. Thus, according to another aspect of the invention, there is provided a method of treatment of benign prostatic hyperplasia which comprises administering a therapeutically effective amount of a compound of the invention to a patient suffering from such a disorder. The use of the compounds of the invention as pharmaceuticals, and the use of the compounds of the invention in the manufacture of a medicament for the treatment of benign prostatic hyperplasia, are also provided.

The compounds of the invention may be administered by any convenient route, for example orally, parenterally (e.g. intravenously, transdermally) or rectally. The daily dose required will of course vary with the particular compound used, the particular condition being treated and with the severity of that condition. However, in general a total daily dose of from about 0.01 to 10 mg/kg of body weight, and preferably about 0.05 to 1 mg/kg, is suitable, administered from 1 to 4 times a day.

The compounds of the invention will generally be administered in the form of a suitable pharmaceutical formulation. Thus, according to another aspect of the invention, there is provided a pharmaceutical formulation including preferably less than 50% by weight of a compound of the invention in admixture with a pharmaceutically acceptable adjuvant, diluent or carrier. The pharmaceutical formulation is preferably in unit dose form. Such forms include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the formulation.

The formulations of the invention may also contain a human 5-a reductase inhibitory compound [see International Patent Application WO 95/28397], or a compound of the invention could be presented in a pharmaceutical pack also containing a human 5-α reductase inhibitory compound as a combined preparation for simultaneous, separate or sequential use.

The compounds of the invention may be tested in the screens set out below.

Contractile Responses of Human Prostate

Prostatic tissue was cut into longitudinal strips (approximately 3×2×10 mm) and suspended in organ baths under a resting tension of 1 g in Krebs Ringer bicarbonate of the following composition (mM): NaCl (119), KCl (4.7), $CaCl_2$ (2.5), $KH_2PO_4$ (1.2), $MgSO_4$ (1.2), $NaHCO_3$ (25), glucose (11), and gassed with 95% $O_2$/5% $CO_2$. The solution also contained 10 mM cocaine and 10 mM corticosterone. Tissues were exposed to a sensitising dose of (−)-noradrenaline (100 mM) and washed over a 45 minute period. Isometric contractions were obtained in response to cumulative additions of (−)-noradrenaline to obtain control curves in all tissues. A further curve was then generated in the presence or absence of antagonist (incubated for 2 hours). Antagonist affinity estimates ($pA_2$) were determined using a single concentration of competing antagonist, $pA_2$=−log [A]/(DR-1) where the dose ratio (DR), relative to corresponding controls, was produced by a single concentration of antagonist [A], assuming competitive antagonism and Schild regression close to unity.

Anaesthetised Dog Model of Prostatic Pressure and Blood Pressure

Mature male beagles (12–15 kg body weight) were anaesthetised with sodium pentobarbitone (30–50 mg/kg i.v.) and a tracheal cannula was inserted. Subsequent anaesthesia was maintained using pentobarbitone infusion. The animals were respirated with air using a Bird Mk8 respirator (Bird Corp., Palm Springs, Calif., U.S.A.) adjusted to maintain blood gasses in the range $pO_2$ 90–110 mm Hg, $pCO_2$ 35–45 mm Hg, pH 7.35–7.45. Body temperature was maintained at 36–37.5° C. using a heated operating table. Catheters were placed into the left femoral artery for recording blood pressure and into the left femoral vein for compound administration. Heart rate was recorded via the lead II E.C.G. A laparotomy was performed to cannulate both ureters to prevent change of fluid volume within the bladder. A 7F cardiac catheter (with a 1.5 ml capacity balloon tip) was inserted into the bladder via the urethra. The balloon was filled with air and the catheter withdrawn until the balloon became lodged in the prostate, which was confirmed by digital pressure. Balloon pressure was recorded via a Druck transducer. Prostatic pressure and haemodynamic parameters were made on a Grass Polygraph (Grass Instruments, Quincy, Mass, U.S.A.) and the data measured on line using a Motorola 68000-based microcomputer system (Motorola Inc., Temple, Ariz., U.S.A.). Compounds were made up in PEG 300 and administered i.v. through a catheter in the femoral vein. Responses to phenylephrine (1–16 μg/kg i.v. in saline) were obtained to generate control dose-response curves (two control curves for each experiment). Compounds were administered (in terms of compound base) at 10–300 μg/kg i.v. 5 min before construction of phenylephrine curves (constructed up to a maximum dose of 128 μg/kg in the presence of test compound).

Due to $\alpha_1$-related dysrhythymic properties of phenylephrine, absolute maximal responses were not obtained but were taken as 10% greater than the control response obtained with 16 μg/kg phenylephrine. Drug concentrations were calculated on the basis of molar weight of compound/kg body weight thus allowing a "pseudo $pA_2$" calculation by Schild analysis using dose ratios derived from shifts in the phenylephrine dose-response curves.

The compounds of the invention may have the advantage that they are more potent, have a longer duration of action, have a broader range of activity, are more stable, have fewer side effects or are more selective (in particular they may have beneficial effects in benign prostatic hyperplasia without causing undesirable cardiovascular effects, for example because they are able to selectively antagonise prostatic subreceptors of the $\alpha_1$-adrenoceptor), or have other more useful properties than the compounds of the prior art.

The invention is illustrated by the following examples, in which the following abbreviations are used:
DMA=dimethylacetamide
DMF=dimethylformamide
DMPU=1,3-dimethyl-3,4,5,6-tetrahydro-2(1H)-pyrimidone
EtOAc=ethyl acetate
EtOH=ethanol
h=hour
MeOH=methanol
min=minute
n-BuOH=n-butanol
THF=tetrahydrofuran
tlc=thin layer chromatography Intermediate 1

1-(t-Butyloxycarbonyl)-1,4-diazepane

To a solution of homopiperazine (10 g, 1.0 mol) and triethylamine (210 ml, 152 g, 1.5 mol) in $CH_2Cl_2$ (500 ml) at 0° C. was added a solution of di-(t-butyl) dicarbonate (195 g, 0.89 mol) in $CH_2Cl_2$ (300 ml). The mixture was allowed to warm to room temperature and stirred for 18 h after which time the $CH_2Cl_2$ was evaporated under reduced pressure. The resulting residue was partitioned between ether and 2N citric acid and the aqueous layer was extracted with ether (4×200 ml). The aqueous layer was basified with 2N aqueous NaOH and then extracted with $CH_2Cl_2$ (4×400 ml). The combined $CH_2Cl_2$ extracts were washed with $H_2O$ (2×), saturated brine (1×) and dried over $MgSO_4$. Evaporation under reduced pressure followed by azeotroping with $CH_2Cl_2$ (4×) gave the title compound as a yellow waxy solid (94.3 g, 53%). $R_f$ 0.25 ($CH_2Cl_2$/MeOH/0.88$NH_3$ 90/10/1, v/v). MS m/z 201 ($MH^+$). Found: C, 58.86; H, 10.03; N, 13.58; $C_{10}H_{20}N_2O_2$ 0.05.$CH_2Cl_2$ requires C, 59.02; H, 9.91; N, 13.70%.

Intermediate 2

1-(t-Butyloxycarbonyl)-4-(4-morpholinecarbonyl)-1,4-diazepane

A solution of Intermediate 1 (92.0 g, 0.46 mol) and triethylamine (96.0 ml, 69.7 g, 0.69 mol) in $CH_2Cl_2$ (500 ml) at 0° C. was treated dropwise with a solution of 4-morpholinecarbonyl chloride (64.0 ml, 82.0 g, 0.55 mol) in $CH_2Cl_2$ (100 ml) and the reaction was stirred at room temperature under $N_2$ for 18 h. The reaction mixture was then diluted with $CH_2Cl_2$ (400 ml) and washed with 2N citric acid (3×400 ml), saturated brine (1×500 ml), dried over $MgSO_4$ and evaporated to give the title compound as an off-white solid (141.7 g, 98%). $R_f$ 0.80 ($CH_2Cl_2$/MeOH/ 0.88$NH_3$ 90/10/1, v/v). MS m/z 314 ($MH^+$). Found: C,57.50; H,8.69; N,13.41; $C_{15}H_{27}N_3O_4$ requires C, 57.50; H, 8.69; N,13.41%.

Intermediate 3

1-(4-Morpholinecarbonyl)-1,4-diazepane hydrochloride

A solution of Intermediate 2 (140.0 g, 0.44 mol) in $CH_2Cl_2$/MeOH (1/1, v/v, 600 ml) at 0° C. was saturated with HCl gas and the reaction mixture was stirred at room temperature under $N_2$ for 18 h after which time the reaction mixture was evaporated under reduced pressure and slurried in EtOAc to give, after filtration, a white hygroscopic solid. This was further purified by slurrying in acetone, filtering, washing with ether and drying in vacuo at 60° C. to give the title compound as a colourless solid (99.0 g, 90%). $R_f$ 0.41 ($CH_2Cl_2$/MeOH/0.88$NH_3$ 84/14/2, v/v). MS m/z 214 ($MH^+$). Found: C, 47.50; H,8.10; N,16.55; $C_{10}H_{19}N_3O_2$ HCl 0.2.$H_2O$ requires C, 47.41; H, 8.12; N,16.59%.

Intermediate 4

1-Acetyl-4-(4-morpholinecarbonyl)-1,4-diazepane

To a solution of Intermediate 3 (50 g, 0.2 mol) and triethylamine (42 ml, 30.5 g, 0.3 mol) in $CH_2Cl_2$ (400 ml) at 5° C. was added acetic anhydride (23 ml, 24.9 g, 0.24 mol) dropwise over 15 min and the reaction was then stirred for a further 2 h at room temperature under $N_2$. Dilution with $CH_2Cl_2$ (600 ml) was followed by washing with saturated aqueous sodium bicarbonate (2×200 ml) and the combined aqueous layers extracted with $CH_2Cl_2$ (1×100 ml). The CH$_2$Cl$_2$ layers were combined and washed with saturated brine, dried over MgSO$_4$ and evaporated to give a light brown oil. This was dissolved in CH$_2$Cl$_2$ (300 ml) and treated with triethylamine (8 ml, 5.8 g, 0.06 mol) and EtOH (5 ml), stirred for 1 h at room temperature then washed with saturated sodium bicarbonate and the aqueous layer extracted with CH$_2$Cl$_2$ (5×). The combined CH$_2$Cl$_2$ layers were dried over MgSO$_4$ and evaporated under reduced pressure to give a yellow oil which was then azeotroped with CH$_2$Cl$_2$ (4×) to give the title compound as a yellow oil (47.1 g, 92%). R$_f$ 0.45 (CH$_2$Cl$_2$/MeOH/0.88NH$_3$ 90/10/1, v/v). MS m/z 256 (MH$^+$). Found: C,52.62; H,8.18; N,15.02; C$_{12}$H$_{21}$N$_3$O$_3$ 0.3.CH$_2$Cl$_2$ requires C, 52.61; H, 7.75; N,14.96%.

EXAMPLE 1

4-Amino-5-(2-chlorophenyl)-7-methoxy-2-[4-(4-morpholinecarbonyl)-1,4-diazepan-1-yl]quinoline (a) 5-(2-Chlorophenyl)-4-cyano-3-nitroanisole 5-Bromo-4-cyano-3-nitroanisole [prepared by the method of Harrison et al, J. Chem. Soc. C, 1769 (1966)] (250 mg, 0.86 mmol) and 2-chlorophenylboronic acid (150 mg, 0.96 mmol) were dissolved in a mixture of toluene (10 ml), EtOH (5.6 ml), and 1N aqueous sodium carbonate (1.7 ml). The solution was placed under a nitrogen atmosphere and tetrakis(triphenylphosphine)palladium (30 mg, 0.03 mmol) added. After refluxing for 3 h, the solvent was removed from the reaction mixture under reduced pressure. The residue was partitioned between H$_2$O (50 ml) and EtOAc (50 ml) and the EtOAc layer washed with H$_2$O (2×50 ml), and dried over MgSO$_4$. Following removal of the solvent, the crude material was purified on silica gel, eluting with hexane/ether (1/1, v/v). This gave the subtitle compound as a colourless gum (252 mg, 100%). R$_f$ 0.38 (hexane/ether 1:1, v/v). MS m/z 306 and 308 (MNH$_4^+$).

(b) 3-Amino-5-(2-chlorophenyl)-4-cyanoanisole

The product of step (a) (300 mg, 11.0 mmol) was dissolved in DMF (3 ml) and a solution of sodium dithionite hydrate added (500 mg, 2.9 mmol in 6 ml of H$_2$O). The solution became warm and some solid precipitated out of solution. After stirring for 30 min at room temperature, 15 ml of H$_2$O and 2N HCl were added. This mixture was extracted with EtOAc (2×30 ml), neutralised using 2N NaOH and re-extracted with EtOAc (2×30 ml). The combined EtOAc extracts were dried over MgSO$_4$ and the solvent removed to give the crude product. This was purified on silica gel, eluting with CH$_2$Cl$_2$/MeOH (98/2, v/v) to give the subtitle compound as colourless gum (190 mg, 74%). R$_f$ 0.29 (hexane/ether 1/1, v/v). MS m/e 276 and 278 (MNH$_4^+$).

(c) 6-(2-chlorophenyl)-4-methoxy-2-{1-[4-(4-morpholinecarbonyl)-1,4-diazepan-1-yl]ethylideneamino}benzonitrile The product of step (b) (190 mg, 0.74 mmol) was dissolved in CH$_2$Cl$_2$ (5 ml) and phosphorous oxychloride (0.082 ml, 0.86 mmol) added in one portion to the stirred solution, at room temperature. After 20 min, a solution of Intermediate 4 (380 mg, 1.5 mmol) in CH$_2$Cl$_2$ (5 ml) was added to the reaction mixture, and the mixture heated to reflux for 14 h. After cooling to room temperature, a further 30 ml of CH$_2$Cl$_2$ was added, and this solution washed with 2N aqueous NaOH (2×20 ml), dried over MgSO$_4$, and the solvent removed to give the subtitle compound as a colourless gum (155 mg, 43%). R$_f$ 0.26 (CH$_2$Cl$_2$/MeOH 95/5, v/v). MS m/z 496 (MH$^+$).

(d) 4-Amino-5-(2-chlorophenyl)-7-methoxy-2-[4-(4-morpholinecarbonyl)-1,4-diazepan-1-yl]quinoline The product of step (c) (155 mg, 0.31 mmol) was dissolved in dry THF (5 ml), under a dry nitrogen atmosphere, and the solution cooled to −78° C. A 1.5M solution of lithium diisopropylamide in THF (0.25 ml, 0.38 mmol) was added to the reaction which was allowed to warm to room temperature. Analysis by tlc indicated that starting material remained, hence the solution was recooled to −78° C. and a further 0.25 ml of the lithium diisopropylamide solution added. After warming to room temperature, the mixture was again analysed by tlc and then quenched with H$_2$O (0.5 ml). EtOAc was added (30 ml) and the solution washed with H$_2$O (2×20 ml), dried over MgSO$_4$, and the solvent removed under reduced pressure. The crude material was purified on silica gel, eluting with CH$_2$Cl$_2$/MeOH/0.88NH$_3$ (92/7/1, v/v) to give the title compound as a white foam (50 mg, 31%). R$_f$ 0.25 (CH$_2$Cl$_2$/MeOH 9/1, v/v). MS m/z 496 (M$^+$). $^1$H NMR (CDCl$_3$) δ: 2.05 (2H, m), 3.14 (2H, m), 3.45 (2H, t), 3.60 (6H, m), 3.70 (2H, t), 3.82 (2H bs), 3.86–3.99 (5H, m), 5.75 (1H, s), 6.47 (1H, s), 7.0 (1H, s), 7.28–7.45 (3H, m), 7.45–7.51 (1H, m). Found C, 60.75; H, 6.02; N, 13.13; C$_{26}$H$_{30}$ClN$_5$O$_3$.0.25 CH$_2$Cl$_2$ requires C,60.96; H, 5.94; N, 13.54%.

EXAMPLE 2

4-Amino-7-methoxy-2-[4-(4-morpholinecarbonyl)-1,4-diazepan-1-yl]-5-phenylquinoline 4-Cyano-3-nitro-5-phenylanisole The subtitle compound was prepared by the method of Example 1(a), but using phenylboronic acid. The crude material was triturated with 20 ml of ether, and recrystallised from EtOAc to give a white crystalline solid (83%). m.p. 175–176° C. R$_f$ 0.44 (hexane/ether 1:1, v/v). MS m/z 169 (no M$^+$ observed).

(b) 3-Amino-4-cyano-5-phenylanisole

Reduction of the product of step (a) using the procedure of Example 1(b) gave the subtitle compound (41%) yellow gum. R$_f$ 0.30 (hexane/ether 1:1, v/v). MS m/z 242 (no M$^+$ observed).

(c) 4-Methoxy-2-{1-[4-(morpholine-4-carbonyl)-1,4-diazepan-1-yl]ethylideneamino}-6-phenylbenzonitrile The subtitle compound was obtained as a white foam from the product of step (b) in 87% yield using the procedure described in Example 1(c). R$_f$ 0.66 (CH$_2$Cl$_2$/MeOH 9/1, v/v). MS m/z 462 (MH$^+$).

(d) 4-Amino-7-methoxy-2-[4-(4-morpholinecarbonyl)-1,4-diazepan-1-yl]-5-phenylquinoline The title compound (87%) was obtained as an off-white powder from the product of step (c) using the procedure described in Example 1(d). R$_f$ 0.16 (CH$_2$Cl$_2$/MeOH 9/1, v/v). MS m/z 462 (MH$^+$). $^1$H NMR (CDCl$_3$) δ: 2.05 (2H, m), 3.16 (4H, m), 3.48 (2H, t), 3.56–3.68 (6H, m), 3.71 (2H, t), 3.87–3.99 (7H, m), 5.73 (1H, s), 6.54 (1H, s), 7.01 (1H, bs), 7.41 (5H, s). Found C, 66.89; H, 6.78; N, 14.42; C$_{26}$H$_{31}$N$_5$O$_3$ 0.1.CH$_2$Cl$_2$ requires C, 66.69; H, 6.69; N, 14.90%

EXAMPLE 3

4-Amino-6,7-dimethoxy-2-[4-(4-morpholinecarbonyl)-1,4-diazepan-1-yl]-5-phenylquinoline (a) 2-(3,4-Dimethoxyphenyl)-4,4-dimethyl-Δ$^2$-oxazoline The subtitle compound was prepared from 3,4-dimethoxybenzoic acid according to the method of Meyers et al., J. Org. Chem., 29, 2787, (1974).

(b) 2-(3,4-Dimethoxy-2-iodophenyl)-4,4-dimethyl-Δ$^2$-oxazoline nButyllithium (2.5M in hexane, 8.9 ml, 22.3 mmol) was added dropwise to a solution of the product of step (a) (4.2 g, 17.8 mmol) in dry ether (200 ml) at 0° C. and the reaction was stirred under $N_2$ for 2 h. This was followed by the dropwise addition of iodine (5.46 g, 21.5 mmol) in ether (100 ml) and the reaction was allowed to warm to room temperature over 1 h. The reaction mixture was poured onto $H_2O$, the ether layer was separated, washed with saturated aqueous sodium thiosulphate solution (1x) followed by saturated brine (1x) then dried over $MgSO_4$ and evaporated under reduced pressure to give the subtitle compound as a yellow oil (5.2 g, 80%). $R_f$ 0.60 ($CH_2Cl_2$/MeOH/0.88$NH_3$ 90/10/1, v/v); MS m/z 362 (MH$^+$).

(c) 3,4-Dimethoxy-2-iodobenzonitrile

To a solution of the product of step (b) (5.2 g, 14.4 mmol) in pyridine (30 ml) was added $POCl_3$ (2.7 ml, 4.4 g, 28.8 mmol) and the reaction was heated to 85° C. for 18 h. The reaction mixture was cooled, partitioned between saturated aqueous sodium carbonate solution (300 ml) and then extracted with ether (2×100 ml). The ether layer was washed with 2N HCl (2×75 ml) followed by $H_2O$ (1x) and then dried over $MgSO_4$ and evaporated under reduced pressure to afford a yellow oil. This was purified by slurrying with hexane and filtering to give the subtitle compound as an off-white solid (2.$^8$2 g, 68%). $R_f$ 0.80 ($CH_2Cl_2$/MeOH 95/5, v/v). MS m/z 307 (MH$^+$). Found: C,38.03; H,2.88; N,4.64; $C_9H_8NO_2I$ 0.05.hexane requires C,38.05; H,2.97; N,4.77%.

(d) 3,4-Dimethoxy-2-iodo-6-nitrobenzonitrile

Nitronium tetrafluoroborate (1.73 g, 13.0 mmol) was added portionwise to a solution of the product of step (c) (2.67 g, 9.2 mmol) in acetonitrile (40 ml) at 0° C. The reaction was stirred for 0.5 h under $N_2$ and then poured into saturated aqueous sodium bicarbonate solution and extracted with EtOAc (1x). The organic layer was washed with saturated brine (1x), dried over $MgSO_4$ and evaporated under reduced pressure to give a residue which was slurried in hexane and filtered to give the subtitle compound as an off-white solid (2.51 g, 82%). $R_f$ 0.46 (EtOAc/hexane 1/1, v/v). MS m/z 352 (MNH$_4^+$).

(e) 3,4-Dimethoxy-6-nitro-2-phenylbenzonitrile

The subtitle compound was prepared from the product of step (d) by the method of Example 1(a) using phenylboronic acid. The subtitle compound (81%) was obtained as a light yellow solid. $R_f$ 0.46 (EtOAc/hexane 1/1, v/v). MS m/z 302 (MNH$_4^+$). Found: C,63.23; H,4.23; N,9.86; $C_{15}H_{12}N_2O_4$ requires C,63.38; H,4.23; N,9.86%.

(f) 6-Amino-3,4-dimethoxy-2-phenylbenzonitrile

The subtitle compound was prepared from the product of step (e) by the method of Example 1(b). The crude product was purified on silica gel, eluting with EtOAc/hexane (1/1, v/v) to give the subtitle compound (60%) as a light yellow solid. $R_f$ 0.40 (EtOAc/hexane 1/1, v/v). MS m/z 272 (MNH$_4^+$). Found: C,70.30; H,5.50; N,10.80; $C_{15}H_{14}N_2O_2$ 0.1.$H_2O$ requires C,70.37; H,5.55; N,10.95%.

(g) 3,4-Dimethoxy-6-{1-[(morpholine-4-carbonyl)-1,4-diazepan-1-yl]ethylideneamino}-2-phenylbenzonitrile The subtitle compound was prepared from the product of step (f) and Intermediate 4 by the method of Example 1(c). The crude product was purified on silica gel, eluting with $CH_2C_2$/4MeOH (95/5, v/v) to give the subtitle compound (87%) as a colourless foam. MS m/z 492 (MH$^+$). Found: C,64.75; H,6.74; N,13.67; $C_{27}H_{33}N_5O_4$ 0.15.$CH_2Cl_2$ requires C,60.64; H,6.61; N,13.89%.

(h) 4-Amino-6,7-dimethoxy-2-[4-(4-morpholinecarbonyl)-1,4-diazepan-1-yl]-5-phenylquinoline The title compound was prepared from the product of step (g) using the method of Example 1(d). The crude product was purified on silica gel, eluting with $CH_2Cl_2$/0.88$NH_3$ (90/10/1, v/v) to give the subtitle compound (46%) as a colourless foam. $R_f$ 0.30 ($CH_2Cl_2$/MeOH/0.88$NH_3$ 90/10/1, v/v). MS m/z 492 (MH$^+$). $^1$H NMR (CDCl$_3$) δ: 2.05 (2H, m), 3.16 (4H, m), 3.35 (2H, m), 3.48 (3H, s), 3.63 (6H, m), 3.74 (2H, m), 3.87 (2H, bs), 3.97 (2H, m), 4.00 (3H, s), 5.68 (1H, s), 7.13 (1H, bs), 7.39 (2H, m), 7.45 (3H, m). Found: C,63.02; H,6.62; N,13.35; $C_{27}H_{33}N_5O_4$ 0.35.$CH_2Cl_2$ requires C,63.02; H,6.47; N,13.44%.

EXAMPLE 4

4-Amino-6,7-dimethoxy-5-(4-fluorophenyl)-2-[4-(4-morpholinecarbonyl)-1,4-diazepan-1-yl]quinoline (a) 3,4-Dimethoxy-2-(4-fluorophenyl)-6-nitrobenzonitrile The subtitle compound was prepared by the method of Example 1(a) from the compound of Example 3(d) and 4-fluorophenylboronic acid. The subtitle compound (83%) was obtained as a light yellow solid. $R_f$ 0.17 (toluene). MS m/z 303 (MH$^+$). Found: C,59.19; H,3.63; N,8.84; $C_{15}H_{12}N_2O_4$ 0.15.$H_2O$ requires C,59.04; H,3.71; N,9.18%.

(b) 6-Amino-34-dimethoxy-2-(4-fluorophenyl)benzonitrile

The subtitle compound was prepared by the method of Example 1(b) from the product of step (a). The subtitle compound (85%) was obtained as a white solid. $R_f$ 0.73 ($CH_2Cl_2$/MeOH/0.88$NH_3$ 90/10/1, v/v). MS m/z 273 (MH$^+$). Found: C,66.09; H,4.79; N,10.28; $C_{15}H_{13}N_2O_2F$ requires C,66.16; H,4.81; N,10.28%.

(c) 3,4-Dimethoxy-2-(4-fluorophenyl)-6-{1-[4-(morpholine-4-carbonyl)-1,4-diazepan-1-yl]ethylideneamino}benzonitrile The subtitle compound was prepared by the method of Example 1(c) from the product of step (b) and Intermediate 4. The subtitle compound (83%) was obtained as a colourless solid. mp 174–176° C. $R_f$ 0.12 (EtOAc). MS m/z 510 (MH$^+$). Found: C,63.61; H,6.35; N,13.68; $C_{27}H_{32}N_5O_4F$ requires C,63.67; H,6.33; N,13.74%.

(d) 4Amino-6,7-dimethoxy-5-(4-fluorophenyl)-2-[4-(4-morpholinecarbonyl)-1,4-diazepan-1-yl]quinoline The title compound was prepared by the method of Example 1(d) from the product of step (c). The crude product was purified on silica gel, eluting with $CH_2Cl_2$/MeOH/0.88$NH_3$ (95/5/0.5, v/v) and then triturated with EtOAc and filtered to give the subtitle compound (41%) as a colourless solid. mp 189–192° C. $R_f$ 0.15 ($CH_2Cl_2$/MeOH/0.88$NH_3$ 95/5/0.5, v/v). MS m/z 510 (MH$^+$). $^1$H NMR (CDCl$_3$) δ: 2.05 (2H, m), 3.13 (4H, m), 3.32 (2H, m), 3.48 (3H, s), 3.63 (6H, m), 3.74 (2H, m), 3.77–4.23 (4H, bm), 4.00 (3H, s), 5.71 (1H, s), 7.15 (2H, m), 7.23 (1H, bs), 7.32 (2H, m). Found: C,63.07; H,6.41; N,13.17; $C_{27}H_{32}N_5O_4F$ 0.25.$H_2O$ 0.15EtOAc requires C,62.82; H,6.39; N,13.28%.

EXAMPLE 5

(R/S)-4-Amino-2-[4-(1,4-benzodioxan-2-carbonyl)-1,4-piperazin-1-yl]-6,7-dimethoxy-5-phenylquinoline (a) 1-Acetyl-4-(t-butyloxycarbonyl)piperazine The subtitle compound was prepared by the methods of Intermediates 1 and 2 but using piperazine in place of homopiperazine and acetyl chloride in place of 4-morpholinecarbonyl chloride.

(b) 6-{1-[4-(t-Butyloxycarbonyl)-1,4-piperazin-1-yl]ethylideneamino}-3,4-dimethoxy-2-phenylbenzonitrile The subtitle compound was prepared by the method of Example 1(c) from the compound of Example 3(f) and the product of step (a). The crude product was purified on silica gel, eluting with $CH_2Cl_2$/MeOH (97/3, v/v). The subtitle compound (96%) was obtained as a foam. $R_f$ 0.35 ($CH_2Cl_2$/MeOH 95/5, v/v). MS m/z 465 (MH$^+$).

(c) 4-Amino-2-[4-(t-butyloxycarbonyl)-1,4-piperazin-1-yl]-6,7-dimethoxy-5-phenylquinoline To a solution of the product of step (b) (270 mg, 0.58 mmol) in DMSO (3 ml) was added KOH flake (33 mg, 0.58 mmol) and the reaction mixture heated to 90° C. for 4 h after which time the reaction was cooled, poured onto $H_2O$ and extracted with EtOAc (3×). The combined organic layers were dried over $MgSO_4$ and evaporated under reduced pressure to give the subtitle compound as a foam (65 mg, 24%). $R_f$ 0.15 ($CH_2Cl_2$/MeOH 95/5, v/v). MS m/z 465 ($MH^+$).

(d) 4-Amino-6,7-dimethoxy-5-phenyl-2-(1,4-piperazin-1-yl)quinoline

HCl was bubbled through a solution of the product of step (c) (580 mg, 1.25 mmol) in $CH_2Cl_2$ at 0° C. After 15 min the reaction mixture was evaporated under reduced pressure and the residue was purified on silica gel, eluting initially with $CH_2Cl_2$/MeOH/0.88$NH_3$ (92/7/1, v/v) followed by $CH_2Cl_2$/MeOH/0.88$NH_3$ (90/10/1) to give the subtitle compound as a light brown foam (380 mg, 84%). $R_f$ 0.16 ($CH_2Cl_2$/MeOH/0.88$NH_3$ 92/7/1, v/v). MS m/z 365 ($MH^+$).

(e) (R/S)-4-Amino-2-[4-(1,4-benzodioxan-2-carbonyl)-1,4-piperazin-1-yl]-6,7-dimethoxy-5-phenylquinoline (R/S)-1,4-Benzodioxan-2-carboxylic acid (50 mg, 0.28 mmol) was added to a solution of 1-hydroxybenzotriazole monohydrate (40 mg, 0.30 mmol) and 1-(3-dimethylaminopropyl)-3-ethylcarbodiimide hydrochloride (70 mg, 0.38 mmol) in $CH_2Cl_2$. This was followed by the sequential addition of 4-methylmorpholine (0.6 ml, 0.55 mmol) and the product of step (d) (100 mg, 0.28 mmol) and the reaction mixture was stirred at room temperature under $N_2$ for 20 h after which time it was washed with $H_2O$, saturated aqueous sodium bicarbonate and then saturated brine. The organic layer was separated, dried over $MgSO_4$ and evaporated under reduced pressure. The crude product was purified on silica gel, eluting initially with EtOAc/hexane (1/1, v/v) followed by EtOAc to give the title compound as a foam (120 mg, 79%). $R_f$ 0.30 (EtOAc/hexane 1/1, v/v). MS m/z 527 ($MH^+$). $^1H$ NMR ($CDCl_3$) δ: 3.41–4.05 (2H, b) 3.52 (3H, s), 3.73 (4H, m) 3.90 (4H, m), 4.00 (3H, s), 4.35 (1H, dd), 4.50 (1H, dd), 4.87 (1H, dd), 5.80 (1H, s), 6.89 (4H, m), 7.16 (1H, m), 7.42 (5H, m). Found: C,66.08; H,5.94; N,9.64; $C_{30}H_{30}N_4O_5$ 0.5.EtOAc 0.5.$H_2O$ requires C,66.25; H,6.04; N,9.66%.

EXAMPLE 6

4-Amino-2-[4-(furan-2-carbonyl)-1,4-piperazin-1-yl]-6,7-dimethoxy-5-phenylquinoline The title compound was prepared by the method of Example 5(e) from the compound of Example 5(d) and 2-furancarboxylic acid. The title compound (74%) was obtained as a foam. $R_f$ 0.30 (EtOAc/hexane 1/1, v/v). MS m/z 459 ($MH^+$). $^1H$ NMR ($CDCl_3$) δ: 3.41–4.05 (2H, b), 3.52 (3H, s), 3.73 (4H, m), 3.90 (4H, m), 4.00 (31H, s), 4.35 (1H, dd), 4.50 (1H, dd), 4.87 (1H, dd), 5.80 (1H, s), 6.89 (4H, m), 7.16 (1H, m), 7.42 (5H, m). Found: C,65.03; H,5.92; N,11.03; $C_{30}H_{30}N_4O_5$ 0.4.EtOAc $H_2O$ requires C,64.73; H,6.10; N,10.94%.

EXAMPLE 7

(R/S)-4-Amino-6,7-dimethoxy-5-phenyl-2-[4-(tetrahydrofuran-2-carbonyl)-j 1,4-piperazin-1-yl]quinoline The title compound was prepared by the method of Example 5(e) from the compound of Example 5(d) and (R/S)-tetrahydrofuran-2-carboxylic acid. The crude product was purified on silica gel eluting with $CH_2Cl_2$/MeOH/0.88$NH_3$ (95/4.5/0.5, v/v) to give the title compound (53%) as a white foam. $R_f$ 0.45 ($CH_2Cl_2$/MeOH/0.88$NH_3$ 92/7/1, v/v). MS m/z 463 ($MH^+$). $^1H$ NMR ($CDCl_3$) δ: 1.82–2.05 (3H, m), 2.35 (11H, m), 3.20–4.00 (12H, m), 3.48 (3H, s), 4.00 (3H, s), 4.63 (1H, m), 5.78 (1H, s), 7.10 (1H, s), 7.35–7.48 (5H, m). Found: C,65.57; H,6.51; N,11.60; $C_{26}H_{30}N_4O_4$ 0.2.$CH_2Cl_2$ requires C,65.62; H,6.39; N,11.68%.

EXAMPLE 8

4-Amino-6,7-dimethoxy-2-[4-(furan-2-carbonyl)-1,4-diazepan-1-yl]-5-phenylquinoline (a) 1-Acetyl-4-(t-butyloxycarbonyl)-1,4-diazepane The subtitle compound was prepared by the methods of Intermediates 1 and 2 but using acetyl chloride in place of 4-morpholinecarbonyl chloride. The subtitle compound (82%) was obtained as a yellow oil. $R_f$ 0.28 ($CH_2Cl$/MeOH 95/5, v/v). MS m/z 243 ($MH^+$).

(b) 6-{-[4-(t-Butyloxycarbonyl)-1,4-diazepan-1-yl]ethyhlideneamino}-3,4-dimethoxy-2-phenylbenzonitrile The subtitle compound was prepared by the method of Example 1(c) from the compound of Example 3(f) and the product of step (a). The subtitle compound (41%) was obtained as a pale yellow foam. $R_f$ 0.21 ($CH_2Cl_2$/MeOH 97.5/2.5, v/v). MS m/z 479 ($MH^+$).

(c) 4-Amino-2-[4-(t-butyloxycarbonyl)-1,4-diazepan-1-yl]-6,7-dimethoxy-5-phenylquinoline The subtitle compound was prepared by the method of Example 1(d) from the product of step (b). The subtitle compound (63%) was obtained as a pale orange foam. $R_f$ 0.51 ($CH_2Cl_2$/MeOH/0.88$NH_3$ 92/7/1, v/v). MS m/z 479 ($MH^+$).

(d) 4-Amino-6,7-dimethoxy-2-(1,4-diazepan-1-yl)-5-phenylquinoline

The subtitle compound was prepared by the method of Example 5(d) from the product of step (c). The subtitle compound was obtained in quantitative yield as a pale orange solid. $R_f$ 0.07 ($CH2Cl_2$/MeOH/0.88$NH_3$ 92/7/1, v/v). MS m/z 379 ($MH^+$).

(e) 4-Amino-6,7-dimethoxy-2-[4-(furan-2-carbonyl)-1,4-diazepan-1-yl]-5-phenylquinoline The title compound was prepared by the method of Example 5(e) from the product of step (d) and 2-furancarboxylic acid. The product was purified by slurrying in EtOAc to give the title compound (72%) as a white solid. $R_f$ 0.58 ($CH_2Cl_2$/MeOH/0.88$NH_3$ 92/7/1, v/v). MS m/z 473 ($MH^+$). $^1H$ NMR ($CDCl_3$) δ: 2.10 (2H, m), 3.50 (3H, s), 3.74 (4H, m), 3.81 (2H, m), 4.00 (8H, m), 5.71 (1H, s), 6.45 (1H, s), 7.01 (1H, bs), 7.65 (1H, bs), 7.44 (5H, m). Found: C,67.57; H,5.90; N,11.63; $C_{27}H_{28}N_4O_4$ 0.5$H_2O$ requires C,67.34; H,6.07; N,11.63%.

EXAMPLE 9

4-Amino-6,7-dimethoxy-5-phenyl-2-[4-(tetrahydropyran-4-carbonyl)-1,4-diazepan-1-yl]quinoline The title compound was prepared by the method of Example 5(e) from the compound of Example 5(d) and tetrahydropyran-4-carboxylic acid. The crude product was purified on silica gel, eluting with $CH_2Cl_2$/MeOH (90/10, v/v) to give the title compound (44%) as a white solid. $R_f$ 0.41 ($CH_2Cl_2$1MeOH/0.88$NH_3$ 90/10/1, v/v). MS m/z 491 ($MH^+$). $^1H$ NMR ($CDCl_3$) δ: 1.74 (1H, m) 1.84–2.15 (3H, m), 2.68 (1H, m), 3.21 (1H, m), 3.50(8H, m), 3.80 (7H, m), 4.01 (5H, m), 5.68 (1H, s), 7.65 (1H, bs), 7.21–7.55 (6H, m). Found: C,66.97; H,7.09; N,10.77; $C_{28}H_{34}N_4O_4$ 0.75$H_2O$ requires C,66.71; H,7.10; N,11.11%.

EXAMPLE 10

4-Amino-5-(,4-chlorophenyl)-6,7-dimethoxy-2-[4-(4-morpholinecarbonyl-1,4-diazepan-1-yl]quinoline (a) 6-Amino-3,4-dimethoxy-2-iodobenzonitrile The subtitle compound was prepared by the method of Example 2(b) from the compound of Example 3(d). The subtitle compound (81%) was obtained as a colourless solid. $R_f$ 0.55 (EtOAc/hexane 1/1, v/v). MS m/z 322 ($MNH_4^+$).

b) 3,4-Dimethoxy-2-iodo-6-{1-[4-(4-morpholinecarbonyl)-1,4-diazepan-1-yl]ethlideneamino}benzonitrile The subtitle compound was prepared by the method of Example 1(c) from the product of step (a) and Intermediate 4. The crude product was purified on silica gel, eluting with $CH_2Cl_2$/MeOH (97/3, v/v) to give the subtitle compound (87%) as a colourless solid. $R_f$ 0.15 ($CH_2Cl_2$). MS m/z 542 ($MH^+$). Found: C,46.00; H,5.17; N,12.44; $C_{21}H_{28}N_5O_4I$ 0.1.$CH_2Cl_2$ requires C,46.08; H,5.17; N,12.74%.

(c) 4-Amino-6,7-dimethoxy-5-iodo-2-[4-(4-morpholinecarbonyl)-1,4-diazepan-1-yl]quinoline The subtitle compound was prepared by the method of Example 1(d) from the product of step (b) except that the reaction was carried out in THF/DMPU (5/1, v/v). The crude product was purified on silica gel, eluting with $CH_2Cl_2$/MeOH (98/2, v/v). The subtitle compound (65%) was obtained as a light brown solid. $R_f$ 0.50 ($CH_2Cl_2$/MeOH/ 0.88$NH_3$ 90/10/1, v/v). MS m/z 542 ($MH^+$). Found: C,45.71; H,5.26; N,12.44; $C_{21}H_{28}N_5O_4I$ 0.25.$CH_2Cl_2$ requires C,45.37; H,5.07; N,12.46%.

(d) 4-Amino-5-(4-chlorophenyl)-6,7-dimethoxy-2-[4-(4-morpholinecarbonyl)-1,4-diazepan-1-yl]quinoline The title compound was prepared by the method of Example 1(a) from the product of step (c) and 4-chlorophenylboronic acid. The crude product was purified on silica gel, eluting with $CH_2Cl_2$/MeOH/0.88$NH_3$ (90/10/1, v/v). The title compound (40%) was obtained as a pale yellow foam. $R_f$ 0.45 ($CH_2Cl_2$/MeOH/0.88$NH_3$ 90/10/1, v/v). MS m/z 526, 528 ($MH^+$). $^1H$ NMR ($CDCl_3$) δ: 2.06 (2H, m), 3.15 (4H, m), 3.35 (2H, m), 3.50 (3H, s), 3.53–3.68 (6H, m), 3.74 (2H, m), 3.97 (5H, m), 4.32 (2H, bs), 5.71 (1H, s), 7.29 (2H, d), 7.45 (2H, d), 7.69 (1H, bs). Found: C,57.34; H,5.71; N,10.97; $C_{27}H_{33}N_5O_4Cl$ 0.67.$CH_2Cl_2$ requires C,57.02; H,5.76; N,12.02%.

EXAMPLE 11

4-Amino-5-(3,5-dichlorophenyl)-6,7-dimethoxy-2-[4-(4-morpholinecarbonyl)-1,4-diazepan-1-yl] quinoline The title compound was prepared by the method of Example 1(a) from the compound of Example 10(c) and 3,5-dichlorophenylboronic acid. The crude product was purified on silica gel, eluting with $CH_2Cl_2$/MeOH/0.88$NH_3$ (90/10/1, v/v). The title compound (24%) was obtained as a pale yellow foam. $R_f$ 0.50 ($CH_2Cl_2$/MeOH/0.88$NH_3$ 90/10/ 1, v/v). MS m/z 560, 562, 564 ($MH^+$). $^1H$ NMR ($CDCl_3$) δ: 2.06 (2H, m), 3.15 (4H, m), 3.35 (2H, m), 3.55 (3H, s), 3.65 (6H, m), 3.74 (2H, m), 3.99 (7H, m), 5.76 (1H, s), 7.10–7.55 (3H, m), 7.45 (1H, s). Found: C,54.04; H,5.31; N,10.70; $C_{27}H_{32}N_5O_4Cl_2$ 0.6.$CH_2Cl_2$ 0.6.MeOH requires C,53.64; H,5.49; N,11.10%.

EXAMPLE 12

4-Amino-6,7-dimethoxy-5-(4-methoxyphenyl)-2-[4-(4-morpholinecarbonyl)-1,4-diazepan-1-yl]quinoline The title compound was prepared by the method of Example 1(a) from the compound of Example 10(c) and 4-methoxyphenylboronic acid. The crude product was purified on silica gel, eluting with $CH_2Cl_2$/MeOH (95/5, v/v). The title compound (30%) was obtained as a pale yellow foam. $R_f$ 0.20 ($CH_2Cl_2$/MeOH 9/1, v/v). MS m/z 522 ($MH^+$). $^1H$ NMR ($CDCl_3$) δ: 2.06 (2H, m), 3.16 (4H, m), 3.35 (2H, m), 3.50 (3H, s), 3.53–3.80 (8H, m), 3.80–4.13 (4H, m), 3.90 (6H, s), 5.71 (1H, bs), 7.00 (2H, d), 7.06 (1H, bs), 7.31 (2H, d). Found: C,61.75; H,6.63; N,12.34; $C_{28}H_{35}N_5O_5$ 0.2.$CH_2Cl_2$ 0.7.$H_2O$ requires C,61.45; H,6.73; N,12.71%.

EXAMPLE 13

4-Amino-5-[35-bis(trifluoromethyl)phenyl]-6,7-dimethoxy-2-[4-(4-morpholinecarbonyl)-1,4-diazepan-1-yl]quinoline The title compound was prepared by the method of Example 1(a) from the compound of Example 10(c) and 3,5-bis(trifluoromethyl)phenylboronic acid. The crude product was purified on silica gel, eluting with $CH_2Cl_2$/MeOH/ 0.88$NH_3$ (90/10/1, v/v). The title compound (24%) was obtained as a pale yellow foam. $R_f$ 0.50 ($CH_2Cl_2$/MeOH/ 0.88$NH_3$ 90/10/1, v/v). MS m/z 628 ($MH^+$). $^1H$ NMR ($CDCl_3$) δ: 2.06 (2H, m), 3.16 (4H, m), 3.35 (2H, m), 3.48 (3H, s), 3.61 (6H, m), 3.77 (2H, m), 4.00 (7H, m), 5.80 (1H, s), 7.10 (1H, bs), 7.84 (2H, s), 7.95 (1H, s). Found: C,53.51; H,5.06; N,10.03; $C_{29}H_{31}N_5O_4F_6$ 0.4.$CH_2Cl_2$ 0.3.MeOH requires C,53.10; H,4.92; N,10.43%.

EXAMPLE 14

4-Amino-6,7-dimethoxy-2-[4-(4-morpholinecarbonyl)-1,4-diazepan-1-yl]-5-[(4-trifluoromethyl)phenyl]quinoline The title compound was prepared by the method of Example 1(a) from the compound of Example 10(c) and 4-(trifluoromethyl)phenylboronic acid. The crude product was purified on silica gel, eluting with $CH_2Cl_2$/MeOH/ 0.88$NH_3$ (90/10/1, v/v). The title compound (10%) was obtained as a pale yellow foam. $R_f$ 0.45 ($CH_2Cl_2$/MeOH/ 0.88$NH_3$ 90/10/1, v/v). MS m/z 560 ($MH^+$). $^1H$ NMR ($CDCl_3$) δ: 2.06 (2H, m), 3.03–4.13 (2H, b), 3.13 (4H, m), 3.34 (2H, m), 3.48 (3H, s), 3.65 (6H, m), 3.76 (2H, m), 4.03 (5H, m), 5.74 (1H, s), 7.16 (1H, bs), 7.50 (2H, d), 7.71 (2H, d). Found: C,56.46; H,5.78; N,11.43; $C_{28}H_{32}N_5O_4F_3$ 0.5.$CH_2Cl_2$ requires C,56.85; H,5.52; N,11.63%.

EXAMPLE 15

4-Amino-5-(3-chlorophenyl)-6,7-dimethoxy-2-[4-(4-morpholinecarbonyl)-1,4-diazepan-1-yl]quinoline The title compound was prepared by the method of Example 1(a) from the compound of Example 10(c) and 3-chlorophenylboronic acid. The crude product was purified on silica gel, eluting with $CH_2Cl_2$/MeOH/0.88 $NH_3$ (90/10/ 1, v/v) followed by trituration with ether. The title compound (43%) was obtained as a colourless foam. $R_f$ 0.34 ($CH_2Cl_2$/ MeOH/0.88 $NH_3$ 90/10/1, v/v); MS in/z 526, 528 ($MH^+$). $^1H$ NMR ($CDCl_3$) δ 2.06 (2H, m), 3.15 (4H, m), 3.35 (2H, m), 3.52 (3H, s), 3.40–3.80 (8H, m), 3.99 (7H, m), 5.77 (1H, s), 7.10–7.50 (4H, m), 7.23 (1H, s). Found: C,59.82; H,6.58; N,11.96. $C_{27}H_{32}N_5O_4Cl$ 0.25.$CH_2Cl_2$ 0.5.ether requires C,60.11; H,6.47; N,11.99%.

EXAMPLE 16

4-Amino-6,7-dimethoxy-2-[4-(4-morpholinecarbonyl-1,4-diazepan-1-yl]-5-phenylquinazoline (a) 2,4-Dichloro-6,7-dimethoxy-5-nitroquinazoline To a suspension of 2,4-dichloro-6,7-dimethoxyquinazoline (30.0 g, 0.12 mol) in acetonitrile (550 ml) at 0° C. was added nitronium tetrafluoroborate (25.9 g, 0.19 mol) portionwise over 15 min. The reaction was stirred for 0.75 h and then evaporated under reduced pressure. The resulting solid was suspended in a mixture of saturated aqueous sodium bicarbonate and EtOAc and the solid filtered, dissolved in $CH_2Cl_2$, dried over $MgSO_4$ and evaporated to give the subtitle compound as a pale yellow solid (27 g). Further material was obtained by separating the organic layer of the filtrate, washing with $H_2O$ (1×), saturated brine (1×), drying over $MgSO_4$ and filtering through a pad of silica. Subsequent evaporation under reduced pressure, trituration with EtOAc and filtration gave the subtitle compound as a pale yellow solid (3.9 g, overall yield 88%). $R_f$ 0.24 (ether/hexane 1/1, v/v).

(b) 2,4-Dihydroxy-6,7-dimethoxy-5-nitroquinazoline

The product of step (a) (27.3 g, 90 mmol) was suspended in a mixture of glacial acetic acid (150 ml) and $H_2O$ (5 ml) and the reaction mixture was heated to 150° C. for 0.5 h after which time a further portion of $H_2O$ (5 ml) was added and heating continued. After a total of 1.5 h heating, a third portion of $H_2O$ (5 ml) was added and heating maintained for a further 0.5 h. The reaction mixture was then cooled and the solid was filtered, washed with ether and dried in vacuo at 80° C. to give the subtitle compound as a pale yellow solid (22.2 g, 93%). $R_f$ 0.38 (EtOAc/MeOH 95/5, v/v). MS m/z 285 ($MNH_4^+$).

(c) 5-Amino-2,4-dihydroxy-6,7-dimethoxyquinazoline

A mixture of the product of step (b) (35.0 g, 0.13 mol) and 10% palladium on carbon (4.0 g) was suspended in glacial acetic acid (200 ml) and hydrogenated at 50 psi (3.4 atm) and 50° C. for 2.5 days. The reaction was then cooled, suspended in $MeOH/CH_2Cl_2$ (1/1,v/v, 1L) and filtered. The residue was transferred to a soxhlet apparatus and continually extracted with MeOH for 3 days. Evaporation afforded a grey solid which was dissolved in 2N NaOH, filtered through a pad of silica, washing with $H_2O$. The filtrate was then acidified with concentrated HCl. The resulting precipitate was isolated by filtration, washing sequentially with $H_2O$ and acetone, then dried in vacuo at 60° C. to give the subtitle compound as a white solid (22.7 g, 73%). $R_f$ 0.42 (EtOAc/MeOH 95/5, v/v). MS m/z 238 ($MH^+$).

(d) 2,4-Dihydroxy-6,7-dimethoxy-5-iodoquinazoline

To a suspension of the product of step (c) (5.5 g, 23.2 mmol) in concentrated HCl (10 ml) at −10° C. was added $H_2O$ (10 ml), followed by an aqueous solution of sodium nitrite (2.4 g, 34.8 mmol in 10 ml), the temperature being maintained below 0° C. The resultant yellow diazonium salt was cautiously added to a solution of potassium iodide (40.0 g, 0.23 mol), copper (I) iodide (4.4 g, 23 mmol) in $H_2O$ (100 ml) heated to 90° C. and heating was maintained after the addition was complete until gas evolution ceased. The mixture was then cooled, filtered and the solid residue washed sequentially with $H_2O$ and aqueous sodium thiosulphate. The crude product was purified on silica gel, eluting initially with EtOAc/MeOH (95/5, v/v) followed by EtOAc/MeOH/AcOH (95/5/1, v/v) affording a solid which was suspended in MeOH and filtered to give the subtitle compound as a yellow/orange solid (2.2 g, 27%) which was contaminated with the compound of step (b) (0.4 g). $R_f$ 0.16 ($CH_2Cl_2$/MeOH 95/5, v/v). MS m/z 366 ($MNH_4^+$).

(e) 2,4-Dihydroxy-6,7-dimethoxy-5-phenylquinazoline

The subtitle compound was prepared by the method of Example 1(a) from the product of step (d) (5.7/1 mixture of compounds, w/w) and phenylboronic acid. The crude product was purified on silica gel eluting with $CH_2Cl_2$/MeOH (95/5, v/v) to give the subtitle compound (95%) as an orange powder which was contaminated (5% w/w) with the compound of step (b). $R_f$ 0.16 ($CH_2Cl_2$/MeOH 95/5, v/v). MS m/z 299 ($MH^+$).

(f) 2,4-Dichloro-6,7-dimethoxy-5-phenylquinazoline

The mixture produced in step (e) (95/5, w/w, 1.75 g, 5.6 mmol of the subtitle compound of step (e)) was suspended in $POCl_3$ (10 ml, 16.5 g, 109 mmol) and the mixture treated with N,N-dimethylaniline (1.86 ml, 1.79 g, 14.7 mmol) and heated at reflux for 1.5 h. After cooling, excess $POCl_3$ was evaporated under reduced pressure and the residue azeotroped with toluene (2×) then partitioned between EtOAc and $H_2O$. The organic layer was separated and washed sequentially with $H_2O$ (3×), saturated brine (1×), dried over $MgSO_4$ and filtered through a pad of silica, washing with EtOAc to give, on evaporation, the subtitle compound as a yellow gum. $R_f$ 0.83 (EtOAc).

(g) 4-Amino-2-chloro-6,7-dimethoxy-5-phenylquinazoline

The product of step (f) was suspended in a saturated solution of ammonia in MeOH and the reaction was stirred under $N_2$ for 3 h after which time $CH_2Cl_2$ was added until all the solid present dissolved. The reaction mixture was then stirred for a further 2.5 days at room temperature, the solvent removed under reduced pressure and the resulting solid suspended in MeOH and isolated by filtration, washing with ether and then drying in vacuo at 60° C. This gave the subtitle compound as a white solid (1.12 g, 65% from the product of step (e)). $R_f$ 0.39 (EtOAc). MS m/z 316, 318 ($MH^+$).

(h) 4-Amino-6,7-dimethoxy-2-[4-(4-morpholinecarbonyl)-1,4-diazepan-1-yl]-5-phenylquinazoline To a solution of the product of step (g) (200 mg, 0.63 mmol) in n-BuOH (10 ml) was added Intermediate 3 (250 mg, 1.0 mmol) and triethylamine (0.22 ml, 160 mg, 1.58 mmol) and the reaction heated to 100° C. under $N_2$ for 18 h. After cooling, the reaction mixture was partitioned between EtOAc and 2N NaOH, the organic layer separated, washed with saturated brine, dried over $MgSO_4$ and evaporated under reduced pressure. The crude product was purified on silica gel, eluting with EtOAc and the resulting solid was then suspended in a minimal volume of EtOAc, filtered and dried in vacuo at 60° C. to give the title compound as a white solid (180 mg, 58%). $R_f$ 0.40 (EtOAc/MeOH 95/5, v/v). MS m/z 493 ($MH^+$). $^1H$ NMR ($CDCl_3$) δ: 2.00 (2H, m), 3.16 (4H, m), 3.35 (2H, m), 3.48 (3H, s), 3.52 (2H, m), 3.65 (4H, m), 3.84 (2H, m), 3.94 (2H, m), 3.97 (3H, s), 4.52 (2H, bs), 6.92 (1H, s), 7.35 (2H, m), 7.40–7.52 (3H, m). Found: C,62.82; 6.52; N,16.70; $C_{26}H_{32}N_6O_4$ 0.25.$H_2O$ requires C,62.85; H,6.59; N,16.91%.

Alternative Route to 4-Amino-2-chloro-6,7-dimethoxy-5-phenylquinazoline [the Compound of Step (g)]

(Aa) 4-Amino-6,7-dimethoxy-2-hydroxy-5-phenylquinazoline

Trifluoroacetic acid (8.1 ml, 0.10 mol) was added dropwise to a stirred solution of the compound of Example 3(f) (12.9 g, 0.051 mol) and sodium cyanate (6.6 g, 0.10 mol) in $CH_2Cl_2$ (200 ml) and the reaction was left to stir at room temperature under $N_2$ for 18 h, after which time an orange precipitate was formed. The solid was isolated by filtration, washing with hexane, dried by suction and then combined with a mixture of 2N aqueous NaOH (250 ml) and MeOH (250 ml). The mixture was heated on a steam bath until the solid had dissolved and after cooling, the solution was acidified with concentrated HCl and warmed on a steam bath until dissolution was complete. The solution was cooled and neutralised with $K_2CO_3$ and the precipitated solid was isolated by filtration, washing with $H_2O$, MeOH, $CH_2Cl_2$ and finally ether to give the subtitle compound as a colourless solid (12.4 g, 82%). MS ml/z 298 (MH$^+$).

(Ab) 4-Amino-2-chloro-6,7-dimethoxy-2-hydroxy-5-phenylquinazoline

DMF (6.4 ml, 0.083 mol) was added dropwise to POCl$_3$ (19.3 ml, 0.21 mol). Once the mixture had cooled, the product of step (Aa) (12.34 g, 0.042 mol) was added and the temperature was maintained at 90° C. for 3 h and then stirred at room temperature for 18 h after which time, the reaction was cautiously quenched with ice. The reaction was then basified with excess 2N NaOH, the temperature was allowed to reach 60° C. and this was maintained for 1 h. The reaction mixture was then cooled and the precipitate was isolated by filtration and dried in vacuo at 60° C. to afford the subtitle compound as an off-white solid (10.2 g, 78%).

EXAMPLE 17

4-Amino-6,7-dimethoxy-2-{4-[1-(3S,4S-dihydroxypyrrolidine)carbonyl]-1,4-diazepan-1-yl}-5-phenylquinazoline hydrochloride (a) N-Benzyl-3S,4S-bis(t-butyldimethylsilyloxy)pyrrolidine The subtitle compound was prepared by the method of Arakawa et al Chem. Pharm. Bull., 39, 2219 (1991).

(b) 1-{1-(3S,4S-Bis(t-butyldimethylsilyloxy)pyrrolidine)carbonyl}-1,4-diazepane

To a stirred solution of the product of step (a) (12.0 g, 28 mmol) in toluene (150 ml) was added a solution of phosgene in toluene (1.93M, 18 ml, 34 mmol). The resulting suspension was heated at reflux for 6 h after which time the solvent was removed under reduced pressure and the residue redissolved in THF (200 ml). The solution was cooled to 0° C. and then added to a solution of homopiperazine (15.0 g, 150 mmol) in THF (100 ml). The resultant solution was heated to 60° C. for 1 h and stirred at room temperature for 18 h. The solvent was removed under reduced pressure and the residue partitioned between $CH_2Cl_2$ (200 ml) and $H_2O$ (10 ml). The organic layer was washed with saturated brine (50 ml) and dried over $MgSO_4$. The solvent was evaporated under reduced pressure and the crude product was purified on silica gel, eluting initially with $CH_2Cl_2$/MeOH/0.88NH$_3$ (96/3.5/0.5, v/v) followed by $CH_2Cl_2$/MeOH/0.88NH$_3$ (92/7/1, v/v) to give the subtitle compound as an oil which slowly crystallised on standing (7.64 g, 60%). $R_f$ 0.2 ($CH_2Cl_2$/MeOH/0.88NH$_3$ 92/7/1, v/v). MS m/z 459 (MH$^+$).

(c) 4-Amino-6,7-dimethoxy-2-{4-[1-(3S,4S-dihydroxypyrrolidine)carbonyl]-1,4-diazepan-1-yl}-5-phenylquinazoline hydrochloride To a solution of the compound of Example 16(g) (200 mg, 0.63 mmol) and triethylamine (0.22 ml, 1.7 mmol) in n-BuOH (10 ml) was added the product of step (b) (350 mg, 0.76 mmol) and the reaction mixture was heated to 100° C. under $N_2$ for 18 h. The reaction was then cooled and evaporated under reduced pressure and HCl was bubbled through a solution of the residue in $CH_2Cl_2$ for 20 min. The reaction mixture was then evaporated under reduced pressure, partitioned between EtOAc and $H_2O$ and the aqueous layer extracted repeatedly with EtOAc. The aqueous layer was then basified with 2N NaOH, extracted with $CH_2Cl_2$ and the organic layer dried over $MgSO_4$ and evaporated to give a gum which was treated with ethereal HCl. The resulting precipitate was filtered, washing with ether, to give the title compound as a white foam, (210 mg, 61%). $R_f$ 0.1 ($CH_2Cl_2$/MeOH 95/5, v/v). MS m/z 509 (MH$^+$). $^1$H NMR (CDCl$_3$) δ: 1.58–2.23 (2H, bm), 3.03–4.35 (2H, bm), 3.23 (4H, m), 3.48 (3H, s), 3.52 (3H, m), 3.71 (4H, m), 4.02 (3H, s), 4.11 (4H, m), 5.16 (1H, bs), 7.32 (2H, m), 7.52 (3H, m), 8.45 (1H, s), 12.59 (1H, bs). Found: C,55.42; H,6.32; N,13.90; $C_{26}H_{32}N_6O_5$ HCl $H_2O$ 0.5EtOAc requires C,55.40; H,6.48; N,13.84%.

EXAMPLE 18

4-Amino-6,7-dimethoxy-2-[4-(3-hydroxyazetidine-1-carbonyl)-1,4-diazepan-1-yl]-5-phenylquinazoline hydrochloride A suspension of the compound of Example 16(g) (205 mg, 0.65 mmol) in n-BuOH was treated with homopiperazine (1.3 g, 13.0 mmol) and the reaction heated to reflux under $N_2$ for 18 h. After cooling, the reaction mixture was partitioned between EtOAc and 2N NaOH, the organic layer separated, washed with $H_2O$ (5×) then evaporated under reduced pressure azeotroping with toluene (3×) to give a foam (280 mg). This was dissolved in $CH_2Cl_2$ (50 ml), triethylamine (0.11 ml, 0.78 mmol) was added and the solution stirred with 4 Å molecular sieves for 2 h before adding dropwise over 1 h to a solution of triphosgene (68.0 mg, 0.23 mmol) in $CH_2Cl_2$ (10 ml) at −5° C. This was then treated with a fine suspension of 2-azetidinol [prepared according to method of Chatterjee et al, J. Chem. Soc. Chem. Commun., 93 (1968)] (142 mg, 1.3 mmol) and triethylamine (0.32 ml, 2.3 mmol) in THF, pre-stirred with 4 Å molecular sieves for 2 h. The reaction mixture was subsequently stirred for 3 days at room temperature under $N_2$ after which time it was partitioned between $CH_2Cl_2$ and 1N NaOH, the organic layer washed with saturated brine, dried over $MgSO_4$ and evaporated. Purification of the crude product on silica gel, eluting initially with EtOAc/MeOH (95/5, v/v) then $CH_2Cl_2$/MeOH/0.88NH$_3$ (90/10/1) followed by treatment with ethereal HCl gave the title compound as a white foam (153 mg, 46%). MS m/z 479 (MH$^+$). $^1$H NMR (CDCl$_3$) δ: 1.61, 1.84 (2H, two m), 3.10 (1H, m), 3.18–3.40 (3H, m), 3.40–3.73 (4H, m), 3.55 (3H, s), 3.90 (3H, bm), 4.10 (3H, s), 4.35 (2H, bm), 5.03 (0.5H, bm), 5.21 (1H, bs), 5.26 (0.5H, bm), 5.66 (0.5H, bm), 6.58 (0.5H, bm), 7.40 (2H, m), 7.55 (3H, m), 8.50 (1H, bs), 12.97 (1H, bs). Found: C,53.94; H,6.40; N,14.06; $C_{25}H_{30}N_6O_4$ HCl 0.4.ether 2.5H$_2$O requires C,54.14; H,6.78; N,14.25%.

EXAMPLE 19

4-Amino-2-[4-(1,4-benzodioxan-2-carbonyl)-1,4-piperazin-1-yl]-6,7-dimethoxy-5-phenylquinazoline (a) 4-Amino-6,7-dimethoxy-5-phenyl-2-(1,4-piperazin-1-yl)quinazoline To a stirred suspension of the compound of Example 16(g) (420 mg, 1.3 mmol) in n-BuOH (10 ml) was added piperazine (2.29 g, 27 mmol) and the reaction heated to 80° C. for 3 h. After cooling, the reaction mixture was partitioned between EtOAc and 2N NaOH, the organic layer was washed sequentially with $H_2O$ (2×) and saturated brine (1×), then dried over $MgSO_4$ and evaporated under reduced pressure. The residue was azeotroped with toluene (1×) then $CH_2Cl_2$ (2×) to give the subtitle compound as a foam (455 mg, 94%). $R_f$ 0.4 ($CH_2Cl_2$/MeOH/0.88NH$_3$ 90/10/1, v/v). MS m/z 366 (MH$^+$).

(b) (R/S)-4-Amino-2-{4-(1,4-benzodioxan-2-carbonyl)-1,4-piperazin-1-yl}-6,7-dimethoxy-5-phenylquinazoline, The title compound was prepared by the method of Example 5(e) from the product of step (a) and (R/S)-1,4- benzodioxan-2-carboxylic acid. The title compound (61%) was obtained as a foam. $R_f$ 0.69 ($CH_2Cl_2$/MeOH/0.88$NH_3$ 90/10/1, v/v). MS m/z 528 (MH$^+$). $^1$H NMR (CDCl$_3$) δ: 3.42–4.16 (8H, b) 3.48 (3H, s), 4.00 (3H, s), 4.35 (1H, dd), 4.48 (1H, dd), 4.87 (1H, dd), 5.80 (1H, s), 6.89 (4H, m), 6.97 (1H, s), 7.16 (1H, m), 7.39 (2H, m), 7.50 (3H, m). Found: C,64.31; H,5.58; N,12.61; $C_{29}H_{29}N_5O_5$ 0.2.EtOAc 0.5.$H_2O$ requires C,64.54; H,5.70; N,12.63%.

EXAMPLE 20

4-Amino-6,7-dimethoxy-5-(4-fluorophenyl)-2-[4-(4-morpholinecarbonyl)-1,4-diazepan-1-yl]quinazoline (a) 2,4-Dichloro-6,7-dimethoxy-5-iodoquinazoline The subtitle compound was prepared by the method of Example 16(f) from the compound of Example 16(d). The subtitle compound was obtained as a solid (contaminated with 2,4,5-trichloroquinazoline). $R_f$ 0.16 (hexane/EtOAc 4/1, v/v).

(b) 4-Amino-2-chloro-6,7-dimethoxy-5-iodoquinazoline

This was prepared by the method of Example 16(g) from the contaminated product of step (a). The subtitle compound (61% from the compound of Example 16(d)) was obtained as a yellow solid (contaminated with the 5-chloro analogue). $R_f$ 0.11 (hexane/EtOAc 4/1, v/v). MS m/z 366 (MH$^+$).

(c) 4-Amino-6,7-dimethoxy-5-iodo-2-[4-(4-morpholinecarbonyl)-1,4-diazepan-1-yl]quinazoline This was prepared by the method of Example 16(h) from the product of step (b) (3/2 mixture, w/w) and Intermediate 3. The crude product was purified on silica gel, eluting initially with hexane followed by EtOAc/hexane (1/1, v/v). The subtitle compound (28% based on the compound of step (b)) was obtained as an orange foam (contaminated with the 5-chloro analogue). $R_f$ 0.41 (EtOAc). MS m/z 543 (MS$^+$).

(d) 4-Amino-6,7-dimethoxy-5-(4-fluorophenyl)-2-[4-(4-morpholinecarbonyl)-1,4-diazepan-1-yl]quinazoline This was prepared by the method of Example 1(a) from the product of step (c) (1.2/1 mixture, w/w) and 4-fluorophenylboronic acid. The crude product was purified on silica gel, eluting initially with hexane/EtOAc (4/1, v/v) followed by EtOAc. The title compound (63% based on the compound of step (c)) was obtained as a white foam. $R_f$ 0.18 (EtOAc). MS m/z 511 (MH$^+$). $^1$H NMR (CDCl$_3$) δ: 2.00 (2H, m), 3.14 (4H, m), 3.35 (2H, m), 3.48 (3H, s), 3.55 (2H, m), 3.66 (4H, m), 3.84 (2H, m), 3.94 (2H, m), 3.97 (3H, s), 4.52 (2H, bs), 6.90 (1H, bs), 7.16 (2H, m), 7.32 (2H, m). Found: C,60.91; H,6.32; N,15.73; $C_{26}H_{31}N_6O_4F$ 0.2.EtOAc requires C,60.90; H,6.17; N,15.91%.

EXAMPLE 21

4-Amino-6,7-dimethoxy-2-{1-[4-(4-morpholinecarbonyl)piperidine]}-5-phenylquinazoline The title compound was prepared by the method of Example 16(h) from the compound of Example 16(g) and 4-(4-morpholinecarbonyl)piperidine (see U.S. Pat. No. 4,022,791). The crude product was purified by column chromatography on silica gel, eluting with $CH_2Cl_2$/EtOH/ 0.88 $NH_3$ (96/3.5/0.5, v/v). Recrystallisation from EtOAc gave the title compound (25%) as a colourless solid. $R_f$ 0.10 ($CH_2Cl_2$/MeOH/0.88 $NH_3$ 96/3.5/0.5 v/v). MS m/z 478 (MH$^+$). $^1$H NMR (CDCl$_3$) δ: 1.75–1.95 (4H, m), 2.70 (1H, m), 2.90 (2H, m), 3.50 (3H, s), 3.55–3.75 (8H, m), 4.00 (3H, s), 4.60 (2H, m), 6.95 (1H, bs), 7.40 (2H, m), 7.50 (3H, m). Found: C,65.34; H,6.56; N,14.55. $C_{26}H_{31}N_5O_4$ requires C,65.39; H,6.54; N,14.66%.

EXAMPLE 22

4-Amino-2-{4-[1-(3S,4S-dihydroxypyrrolidine) carbonyl)]-1,4-diazepan-1-yl}-6,7-dimethoxy-5-phenylquinoline (a) 6-{1[(4-Benzyl)-1,4-diazepan-1-yl]ethylideneamino}-3,4-dimethoxy-2-phenylbenzonitrile The subtitle compound was prepared by the method of Example 1(c) from the compound of Example 3(f) and 1-acetyl-4-benzyl-1,4-diazepane [Sutton, J. Med. Chem., 13, 1026 (1970)] to give the subtitle compound (83%) as an orange glass. $R_f$ 0.36 ($CH_2Cl_2$/MeOH 95/5, v/v). MS m/z 469 (MH$^+$).

(b) 4-Amino-2-(4-benzyl-1,4-diazepan-1-yl)-6,7-dimethoxy-5-phenylquinoline

A solution of the product of step (a) (440 mg, 0.94 mmol) in dimethoxyethane (10 ml) was treated with potassium t-butoxide (316 mg, 2.82 mmol) and reaction mixture heated at reflux for 5 h. When cool, the mixture was partitioned between EtOAc and $H_2O$. The organic layer was dried over MgSO4 and evaporated at reduced pressured to an oil. Trituration with MeOH and filtration gave the subtitle compound as a pale pink solid, (300 mg, 68%). $R_f$ 0.39 ($CH_2Cl_2$/ MeOH/0.88 $NH_3$ 92/7/1 v/v). $^1$H NMR (CDCl$_3$) δ: 1.95(2H, m), 2.65(2H, m), 2.8(2H, m), 3.5(3H, s), 3.65(3H, s), 3.7–3.9(6H, m), 4.00(3H, s), 5.7(1H, s), 7.1(1H, bs), 7.2–7.35(5H, m), 7.4(5H, m).

(c) 4-Amino-2-(1,4-diazepan-1-yl)-6,7-dimethoxy-5-phenylquinoline

A mixture of the product of step (b) (700 mg, 1.5 mmol), palladium hydroxide (20%w/w, 140 mg) and acetic acid (0.17 ml, 3.0 mmol) in EtOH (30 ml) was hydrogenated at 345 kPa (50 psi) and room temperature for 18 h. The reaction was filtered through Arbocel® and the filtrate evaporated under reduced pressure to yield the subtitle compound as a buff solid (487 mg, 86%). $R_f$ 0.10 ($CH_2Cl_2$/ MeOH/0.88 $NH_3$ 90/10/1, v/v). $^1$H NMR(CDCl$_3$) δ: 1.95 (2H, m), 2.85(2H, m), 3.06(2H, m), 3.50(3H, s), 3.75–3.85 (6H, m), 4.0(3H, s), 5.7(1H, s), 7.15(1H, s), 7.45(5H, m).

(d) 4-Amino-2-(4-chlorocarbonyl-1,4-diazepan-1-yl)-6,7-dimethoxy-5-phenylquinoline To a solution of triphosgene (128 mg, 0.43 mmol) in $CH_2Cl_2$ (10 ml) at −10° C. was added dropwise a solution of the product of step (c) (442 mg, 1.17 mmol) and triethylamine (0.195 ml, 142 mg, 1.4 mmol) in $CH_2Cl_2$ (20 ml) over 1 h. The mixture was stirred at −10° C. for a further 1 h and then evaporated under reduced pressure to yield the subtitle compound as a brown foam (514 mg, 100%) which was used without further treatment.

(e) 4-Amino-2-{4-[1-(3S,4S-dihydroxypyrrolidine) carbonyl)]-1,4-diazepan-1-yl}-6,7-dimethoxy-5-phenylquinoline A mixture of the product of step (d) (257 mg, 0.58 mmol), 3S,4S-bis (t-butyldimethylsilyl-oxy)pyrrolidine [Nagel, Angew. Chem. Int. Ed. Engl., 23, 435 (1984)] (213 mg, 0.64 mmol) and triethylamine (0.098 ml, 71 mg, 0.7 mmol) in THF (20 ml) was refluxed for 18 h. When cool, the mixture was partitioned between EtOAc and aqueous saturated sodium hydrogen carbonate solution. The aqueous layer was washed again with EtOAc and finally $CH_2Cl_2$. The combined organics were dried over MgSO$_4$ and evaporated at reduced pressure. The crude material was purified on silica gel eluting with a gradient eluent of 3–7% MeOH in $CH_2Cl_2$. The purified material was treated with a methanolic solution of HCl [prepared by adding acetyl chloride (0.07 ml) cautiously to MeOH (3 ml)] and stirred at room temperature for 2.5 h. The mixture was basified with aqueous saturated NaHCO$_3$ and evaporated under reduced pressure.

The residue was extracted with $CH_2Cl_2$, the extract evaporated under reduced pressure and the crude product purified on silica gel eluting with $CH_2Cl_2$/MeOH/0.88 $NH_3$ (92/7/1, v/v) to yield the title compound (30 mg, 10%) as a colourless solid. $R_f$ 0.25 ($CH_2Cl_2$/MeOH/0.88$NH_3$ 84/14/2, v/v). MS m/z 508 MH$^+$. $^1$H NMR(d$_6$-DMSO) δ: 1.87(2H, m), 3.12 (2H, m), 3.34(3H, s), 3.4(2H, m), 3.52(3H, m), 3.68–3.9(8H, m), 4.6(2H, bs), 4.87(2H, m), 5.85(1H, s), 6.93(1H, s), 7.3(2H, m), 7.45(3H, m).

EXAMPLE 23

4-Amino-6,7-dimethoxy-2-[4-(4-fluoropiperidinecarbonyl)-1,4-diazepan-1-yl]-5-phenylquinoline A mixture of the compound of Example 22(d) (257 mg, 0.58 mmol), 4-fluoropiperidine hydrochloride, [J. Org. Chem. 44, 771 (1979)] (90 mg, 0.64 mmol) and triethylamine (0.18 ml, 1.29 mmol) in THF (20 ml) was heated at reflux for 18 h. When cool the reaction was evaporated under reduced pressure and then partitioned between EtOAc and saturated aqueous sodium bicarbonate. The organic layer was dried over $MgSO_4$ and evaporated under reduced pressure. Purification on silica gel eluting with a gradient eluent of 3–7% MeOH in $CH_2Cl_2$ afforded the title compound as a foam (102 mg, 35%). $R_f$ 0.31 ($CH_2Cl_2$/MeOH/0.88$NH_3$ 92/7/1, v/v). MS m/z 508 (MH$^+$). NMR (CDCl$_3$) δ: 1.75–1.95(4H, m), 2.05(2H, m), 3.1(2H, m), 3.35(4H, m), 3.45–4.05(12H, m), 4.70 and 4.85(1H, m), 5.70(1H, s), 7.1(1H, bs) 7.45(5H, m). Found: C,64.54; H,6.76; N,12.59. $C_{28}H_{34}N_5O_3F$ 0.5EtOAc 0.5.$H_2O$ requires C,64.27; H,7.01; N,12.49%.

EXAMPLE 24

4-Amino-6,7-dimethoxy-2-[4-(4-morpholinesulphonyl)-1,4-diazepan-1-yl]-5-phenylquinzoline (a) 1-(t-Butyloxycarbonyl)-4-{4-morpholinesulphonyl}-1,4-diazepane The subtitle compound was prepared by the method of Intermediate 2 from Intermediate 1 and 4-morpholinesulphonyl chloride [Repine et al J. Med. Chem., 34, 1935 (1991)]. The reaction mixture was partitioned between $CH_2Cl_2$ and 1N NaOH. The organic phase was washed again with 1N HCl, then $H_2O$ and dried over $MgSO_4$ and evaporated under reduced pressure. Purification on silica gel eluting with $CH_2Cl_2$/MeOH/0.88 $NH_3$ (98/1.25/0.25, v/v) initially and then (96/3.5.0.5, v/v) gave the subtitle compound as a gum (53%). $R_f$ 0.44 ($CH_2Cl_2$/MeOH/0.88 $NH_3$ 96/3.5/0.5, v/v). MS m/z 350 (MH$^+$). $^1$H NMR(CDCl$_3$) δ: 1.4(9H, s), 1.9(2H, m), 3.17(4H, m), 3.22(2H, m), 3.4(2H, m), 3.5(2H, m), 3.73(6H, m).

(b) 1-(4-Morpholinesulphonyl)-1,4-diazepane hydrochloride

The subtitle compound was prepared by the method of Intermediate 3 from the product of step (a). The subtitle compound (97%) was obtained as a white solid. $R_f$ 0.09 ($CH_2Cl_2$/MeOH/0.88 $NH_3$ 92/7/1, v/v). MS m/z 250 (MH$^+$). NMR(d$_6$-DMSO) δ: 2.1(2H, m), 3.1(4H, m), 3.4(4H, m), 3.62(8H, m), 9.2(2H, b).

(c) 4-Amino-6,7-dimethoxy-2-[4-(morpholinesulphonyl)-1,4-diazepan-1-yl])-5-phenylquinazoline The title compound was prepared by the method of Example 16(h) from the product of step (b) and the compound of Example 16(g). The mixture was purified on silica gel eluting with 3% MeOH in $CH_2Cl_2$. Evaporation under reduced pressure and recrystallisation from EtOAc/hexane gave the title compound (33%) as a colourless solid. $R_f$ 0.27 ($CH_2Cl_2$/MeOH 95/5 v/v). MS m/z 529 (MH$^+$). $^1$H NMR (CDCl$_3$) δ: 2.03(2H, m), 3.08(4H, m), 3.37(2H, m), 3.47 (3H, s), 3.53(2H, m), 3.63(4H, m), 3.9(2H, m), 3.95(2H, m), 3.98(3H, s), 4.56(2H, s), 6.9(1H, s), 7.37(2H, m), 7.44(3H, m). Found C, 56.23; H,6.06; N,15.56. $C_{23}H_{32}N_6O_5S$ 0.5.$H_2O$ requires C,56.42; H,6.14; N, 15.79%.

EXAMPLE 25

4-Amino-2-(7-aminosulfonyl-1,2,3,4-tetrahydroisoquinolin-2-yl)-6,7-dimethoxy-5-phenylquinazoline To a solution of the compound of Example 16(g) (500 mg, 1.6 mmol) and triethylamine (0.66 ml, 4.8 mmol) in a mixture of n-BuOH (10 ml) and DMA (3 ml) was added 1,2,3,4 tetrahydroisoquinoline-7-sulfonamide hydrochloride (R.G. Pendleton et al, The Journal of Pharmacology and Experimental Therapeutics, 208, 24, 1979) (597 mg, 2.4 mmol) and the reaction mixture was heated to 100° C. under $N_2$ for 18 h. The reaction was then cooled, partitioned between 2N aqueous NaOH and EtOAc, the organic layer was washed with $H_2O$, dried over $MgSO_4$ and evaporated under reduced pressure. The residue was triturated with ether/hexane and the resulting solid isolated by filtration to give the title compound as a light yellow solid, (360 mg, 46%). $R_f$ 0.62 ($CH_2Cl_2$/MeOH/0.88$NH_3$ 90/10/1, v/v). MS m/z 492 (MH$^+$). $^1$H NMR (D$_6$-DMSO) δ: 2.87 (2H, dd), 3.37 (3H, s), 3.90 (3H, s), 4.00 (2H, dd), 4.94 (2H, s), 6.90 (1H, s), 7.20–7.40 (6H, m), 7.45–7.65 (6H, m). Found: C,60.47; H,5.39, N,13.72; $C_{25}H_{25}N_5O_4S$ 0.3.$H_2O$ requires C,60.42; H,5.19, N, 14.09%.

EXAMPLE 26

4-Amino-6,7-dimethoxy-5-phenyl-2-(3-pyridinemethylamino)quinazoline

To a solution of the compound of Example 16(g) (300 mg, 0.95 mmol) and triethylamine (0.60 ml, 5.7 mmol) in a mixture of n-BuOH (10 ml) and DMA (2 ml) was added 3-(aminomethyl)pyridine and the reaction mixture was heated to 100° C. under $N_2$ for 24 h after which time, a further portion of DMA (2 ml) was added and heating continued for a subsequent day. The reaction was then cooled, partitioned between $H_2O$ and $CH_2Cl_2$, the organic layer was washed with $H_2O$, dried over $MgSO_4$ and evaporated under reduced pressure. The residue was chromatographed on silica, eluting with $CH_2Cl_2$/MeOH/0.88$NH_3$ (90/10/1, v/v) to give the title compound as a colourless foam, (65 mg, 18%). $R_f$ 0.52 ($CH_2Cl_2$/MeOH/0.88$NH_3$ 84/14/2, v/v). MS m/z 388 (MH$^+$). $^1$H NMR (CDCl$_3$) S: 3.45 (2H, dd), 3.97 (3H, s), 4.65 (2H, bs), 4.71 (2H, bs), 5.40 (1H, bs), 6.94 (1H, s), 7.15–7.30 (2H, m), 7.39 (2H, m), 7.50 (3H, m), 7.71 (1H, d), 8.50 (1H, d), 8.61 (1H, s). Found: C,65.48; H,5.51, N,16.68; $C_{22}H_{21}N_5O_2$ 0.1.MeOH 0.25.$CH_2Cl_2$ requires C,65.18; H,5.36, N,17.00%.

EXAMPLE 27

4-Amino-6,7-dimethoxy-5-(4-fluorophenyl)-2-[4-(morpholinecarbonylamino)-1-propaneamino]quinoline To a solution of the compound of Example 4 (150 mg, 0.29 mmol) in THF (5 ml) at 0° C. under $N_2$ was added a 1.5M solution of lithium diisopropylamide in cyclohexane (0.2 ml, 0.3 mmol) and the reaction was allowed to reach room temperature and stirred for 1 h. This was followed by the addition of further portions of lithium diisopropylamide (0.4 ml, 0.6 mmol) and a final portion of lithium diisopropylamide (0.2 ml, 0.3 mmol) after a further 2 h. The reaction was then stirred at room temperature for a further 3 h, after which time it was quenched with $H_2O$, the product extracted into 2N aqueous HCl, the aqueous layer separated, neutralised with sodium bicarbonate, extracted with $CH_2Cl_2$ (3×) dried over $MgSO_4$ and evaporated under reduced pressure. The resulting residue was purified by chromatography on silica, eluting with $CH_2Cl_2$/MeOH/0.88$NH_3$ (90/10/1, v/v) to give the title compound as an off-white solid (82 mg, 58%). $R_f$ 0.17 ($CH_2Cl_2$/MeOH/0.88$NH_3$ 90/10/1, v/v). MS m/z 484 (MH$^+$). $^1$H NMR (CDCl$_3$) δ: 1.95 (2H, m), 3.27 (2H, m), 3.37 (2H, m), 3.48 (3H, s), 3.55 (2H, m), 3.65 (4H, m), 3.90 (5H, bm), 3.99 (3H, s), 5.08 (1H, m), 5.70 (1H, s), 7.03–7.23 (3H, in), 7.31–7.44 (2H, m). Found: C,60.72; H,6.37, N, 13.38; $C_{25}H_{30}N_5O_4F$ 0.35.ether 0.7.$H_2O$ requires C,60.73; H,6.74, N,13.41%

EXAMPLE 28

4-Amino-6,7-dimethoxy-5-(3-fluorophenyl)-2-[L(4-morpholinecarbonyl)-1,4-diazepan-1-yl]quinoline To a solution of the compound of Example 10(b) (200 mg, 0.37 mmol) and 3-fluorophenylboronic acid (62 mg, 0.44 mmol) in a mixture of toluene (9 ml), 1M aqueous $Na_2CO_3$ (1.5 ml) and EtOH (5 ml) was added tetrakis (triphenylphosphine)palladium (13 mg, 0.44 mmol) and the reaction was heated to reflux for 1 h. The reaction was then cooled, partitioned between EtOAc and $H_2O$, the organic layer dried over $MgSO_4$ and evaporated to afford a brown residue. This was dissolved in 1,2-dimethoxyethane, the solution purged with $N_2$ and then potassium t-butoxide (124 mg, 1.1 mmol) was added and the reaction heated to reflux for 1 h. After cooling, the reaction mixture was partitioned between EtOAc and $H_2O$, the organic layer was dried over $MgSO_4$ and evaporated in vacuo. The product was purified by chromatography on silica gel, eluting with $CH_2Cl_2$/MeOH/0.88 $NH_3$ (96/3.5/0.5, v/v) to afford the title compound as a brown foam (136 mg, 72%). $R_f$ 0.39 ($CH_2Cl_2$/MeOH/0.88 $NH_3$ 92/7/1, v/v). MS n/z 510 (MH$^+$). $^1$H NMR (CDCl$_3$) δ: 2.03 (2H, m), 3.16 (4H, m), 3.34 (2H, m), 3.50 (3H, s), 3.59 (2H, m), 3.65 (4H, m), 3.71 (2H, m), 3.80 (2H, bs), 3.94 (2H, m), 3.99 (3H, s), 5.74 (1H, s), 7.06 (1H, bs), 7.10–7.20 (3H, m), 7.41 (1H, s). Found: C,62.70; H,6.22; N,13.18. $C_{27}H_{32}N_5O_4F$ 0.5.$H_2O$ requires C,62.53; H,6.41; N,13.50%.

EXAMPLE 29

4-Amino-6,7-dimethoxy-2-(1-methylpiperidin-4-yl)-5-phenylquinoline

The title compound was prepared by the method of Example 5(e) from the compound of Example 8(d) and 1-methylpiperidine-4-carboxylic acid [Rogers et a/Molecular Pharmacology 36, 333 (1989)]. The product was purified by chromatography on silica gel, eluting with EtOAc/diethylamine (90/10, v/v) to afford the title compound (63%) as an orange solid. $R_f$ 0.15 ($CH_2Cl_2$/MeOH/ 0.88 $NH_3$ 92/7/1, v/v). MS m/z 504 (MH$^+$). $^1$H NMR (CDCl$_3$) δ:1.35 (4H, m), 2.06 (2H, m), 2.23 (3H, s), 2.30 (2H, m), 2.42 (1H, m), 2.80–2.95 (2H, m), 3.50 (3H, s), 3.59 (2H, m), 3.78 (6H, m), 3.95–4.13 (2H, bs), 4.00 (3H, s), 5.68 (1H, s), 7.13 (1H, bs), 7.38 (2H, m), 7.45 (3H, m). Found: C,67.03; H,7.37; N,12.87. $C_{29}H_{37}N_5O_3$ 0.5.$H_2O$ 0.5.EtOAc requires C,66.88; H,7.60; N,12.58%.

EXAMPLE 30

4-Amino-6,7-dimethoxy-2-[3-(morpholinecarbonylamino)ethaneamino]-5-phenylquinazoline (a) 4-Amino-2-(3-aminoethaneamino)-6,7-dimethoxy-5-phenylquinazoline This was prepared by the method of Example 16(h) from the compound of Example 16(g) and 10 mole equivalents of 1,2-ethanediamine, in the presence of catalytic potassium iodide. The subtitle compound (66%) was obtained as a colourless foam. $R_f$ 0.42 ($CH_2Cl_2$/MeOH/0.88$NH_3$ 84/14/2, v/v). MS ma/z 340 (MW).

(b) 4-Amino-6,7-dimethoxy-2-[3-(morpholinecarbonylamino)ethaneamino]-5-phenylquinazoline A solution of the product of step (a) (343 mg, 1.0 mmol) in $CH_2Cl_2$ (3 ml) at 0° C. under $N_2$ was treated with N-methylmorpholine (0.14 ml, 1.3 mmol) followed by the dropwise addition of a solution of 4-morpholinecarbonyl chloride (0.11 ml, 1.1 mmol) in $CH_2Cl_2$ (1 ml). The reaction was allowed to reach room temperature and stirred for 18 h. The reaction was then quenched with $H_2O$, extracted with $CH_2Cl_2$, the organic layer separated, washed with saturated brine, dried over $MgSO_4$ and evaporated. Purification on silica gel, eluting with ($CH_2Cl_2$/MeOH/0.88$NH_3$ 90/10/1, v/v) followed by trituration with ether afforded the title compound as a colourless foam (185 mg, 34%). $R_f$ 0.45 ($CH_2Cl_2$/MeOH/0.88$NH_3$ 90/10/1, v/v). MS m/z 453 (MH$^+$). $^1$H NMR (CDCl$_3$) δ: 3.32–3.80 (13H, m), 4.00 (5H, s), 5.34 (3H, b), 5.94 (1H, bs), 7.03 (1H, bs), 7.32 (2H, m), 7.55 (3H, m). Found: C,53.68; H,6.16; N,16.45; $C_{23}H_{28}N_6O_4$ 0.1.ether $CH_2Cl_2$ requires C,53.77; H,5.73, N,16.43%.

EXAMPLE 31

4-Amino-6,7-dimethoxy-2-[4-(morpholinecarbonylamino)-1-N-methylpropaneamino]-5-phenylquinazoline (a) 4-Amino-2(4-amino-1-N-methylpropaneamino)-6,7-dimethoxy-5-phenylquinazoline This was prepared by the method of Example 16(h) from the compound of Example 16(g) and 10 mole equivalents of N-methyl-1,3-propanediamine, in the presence of catalytic potassium iodide. The subtitle compound (17%) was obtained as a colourless foam. $R_f$ 0.45 ($CH_2Cl_2$/MeOH/ 0.88$NH_3$ 84/14/2, v/v). MS m/z 368 (MH$^+$).

(b) 4-Amino-6,7-dimethoxy-2-[4-(morpholinecarbonylamino)-1-N-methylpropaneamino]-5-phenylquinazoline The title compound was prepared by the method of Example 30(b) from the product of step (a) and 4-morpholinecarbonyl chloride. The crude product was purified on silica gel, eluting with ($CH_2Cl_2$/MeOH/0.88$NH_3$ 90/10/1, v/v) followed by trituration with ether to afford the title compound (49%) as a colourless foam. $R_f$ 0.56 ($CH_2Cl_2$/MeOH/0.88$NH_3$, 90/10/1, v/v). MS m/z 481 (MH$^+$). $^1$H NMR (CDCl$_3$) δ: 1.81 (2H, m), 3.13 (3H, s), 3.32 (6H, m), 3.50 (3H, s), 3.65 (4H, m), 3.84 (2H, m), 4.00 (3H, s), 4.71 (2H, bs), 5.65 (1H, bs), 7.00 (1H, bs), 7.35 (2H, m), 7.48 (3H, m). Found: C,58.84; H,6.68; N,15.69; $C_{25}H_{32}N_6O_4$ 0.2.ether 0.5.$CH_2Cl_2$ requires C,58.72; H,6.56; N,15.63%.

EXAMPLE 32

(R/S)-4-Amino-6,7-dimethoxy-5-phenyl-2-[4-(tetrahydrofuran-2-carbonylamino)-1-N-methylpropaneamino]quinazoline The title compound was prepared by the method of Example 5(e) from the product of Example 31(a) and (R/S)tetrahydrofuran-2-carboxylic acid. The crude product was purified on silica gel, eluting with ($CH_2Cl_2$/MeOH/ 0.88$NH_3$ 90/10/1, v/v) followed by trituration with ether to afford the title compound (57%/O) as a colourless foam. $R_f$ 0.51 ($CH_2Cl_2$/MeOH/0.88$NH_3$ 90/10/1, v/v). MS m/z 466 (MH$^+$). $^1$H NMR (CDCl$_3$) δ: 1.58 (1H, m), 1.71–1.97 (3H, m), 2.23 (2H, m), 2.94 (1H, m), 3.16 (3H, s), 3.39 (1H, m), 3.50 (3H, s), 3.71 (1H, m), 3.84 (1H, m), 3.89–4.05 (2H, m), 4.00 (3H, s), 4.40 (1H, t), 5.15 (2H, b), 7.05 (1H, bs), 7.40 (2H, m), 7.50 (3H, m), 8.39 (1H, bs). Found: C,63.71; H,6.85; N,14.64; $C_{25}H_{31}N_5O_4$ 0.1.$CH_2Cl_2$ requires C,63.59; H,6.63; N,14.77%.

EXAMPLE 33

4-Amino-6,7-dimethoxy-2-[4-(morpholinecarbonylamino)-1-propaneamino]-5-phenylquinazoline (a) 4-Amino-2-(4-amino-1-propaneamino)-6,7-dimethoxy-5-phenylquinazoline The subtitle compound was prepared by the method of Example 16 h) from the compound of Example 16(g) and 10 mole equivalents of 1,3-propanediamine, in the presence of catalytic potassium iodide. The subtitle compound (72%) was obtained as a colourless foam. $R_f$ 0.11 ($CH_2Cl_2$/MeOH/ 0.88$NH_3$ 84/14/2, v/v). MS m/z 354 (MH$^+$).

(b) 4-Amino-6,7-dimethoxy-2-[4-morpholinecarbonylamino)-1-propaneamino]-5-phenylquinazoline The title compound was prepared by the method of Example 30(b) from the product of step (a) and 4-morpholinecarbonyl chloride. The crude product was purified on silica gel, eluting with ($CH_2Cl_2$/MeOH/0.88$NH_3$ 90/10/1, v/v) followed by trituration with ether to afford the title compound (71%) as a colourless solid. $R_f$ 0.40 ($CH_2Cl_2$/ MeOH/0.88$NH_3$ 90/10/1, v/v). MS m/z 467 (MH$^+$). $^1$H NMR (CDCl$_3$) δ: 1.80 (2H, m), 3.39 (6H, m), 3.50 (3H, s), 3.58 (2H, m), 3.68 (4H, m), 4.00 (3H, s), 4.90 (2H, bs), 5.50 (1H, bs), 5.80 (1H, bs), 6.90 (1H, s), 7.37 (2H, m), 7.52 (3H, m). Found: C,58.69; H,6.49; N,16.53; $C_{24}H_{30}N_6O_4$ 0.4.$CH_2Cl_2$ requires C,58.54; H,6.20; N,16.79%.

EXAMPLE 34

(R/S)-4-Amino-6,7-dimethoxy-5-phenyl-2-[4-(tetrahydrofuran-2-carbonylamino)-1-propaneamino] quinazoline The title compound was prepared by the method of Example 5(e) from the product of Example 33(a) and (R/S)-tetrahydrofuran-2-carboxylic acid. The crude product was purified on silica gel, eluting with ($CH_2Cl_2$/MeOH 90/10, v/v) followed by trituration with toluene to afford the title compound (52%) as a colourless foam. $R_f$ 0.70 ($CH_2Cl_2$/MeOH/0.88$NH_3$ 84/14/2, v/v). MS m/z 452 (MH$^+$). $^1$H NMR (CDCl$_3$) δ: 1.67 (2H, m), 1.90 (2H, m), 2.23 (2H, m), 3.06 (1H, m), 3.35 (2H, m), 3.50 (3H, s), 3.61 (2H, m), 3.87 (1H, m), 3.99 (3H, s), 4.01 (1H, bs), 4.40 (1H, t), 5.35 (2H, b), 7.03 (1H, bs), 7.39 (2H, m), 7.52 (3H, m), 8.20 (1H, bs). Found: C,63.18; H,6.50; N,14.66; $C_{24}H_{29}N_5O_4$. 0.1.toluene 0.5.$H_2O$ requires C,63.16; H,6.61; N,14.91%.

EXAMPLE 35

4-Amino-6,7-dimethoxy-5-phenyl-2-[4-(2-pyrimidineamino)-1-propaneamino]quinazoline The product of Example 33(a) (230 mg, 0.65 mmol) was added to a solution of 2-chloropyrimidine (82 mg, 0.72 mmol) and triethylamine (0.11 ml, 0.78 mmol) in a mixture of n-BuOH (3 ml) and DMA (1 ml). The reaction was heated to 80° C. under $N_2$ for 18 h, after which the reaction was cooled, washed with $H_2O$, extracted with $CH_2Cl_2$, then washed with saturated brine. The organic layer was separated and dried over MgSO$_4$ and the product purified by silica gel chromatography, eluting with ($CH_2Cl_2$/MeOH/ 0.88$NH_3$ 90/10/1, v/v) followed by trituration with ether. The title compound was obtained as a colourless foam (110 mg, 34%). $R_f$ 0.57 ($CH_2Cl_2$/MeOH/0.88$NH_3$ 84/14/2, v/v). MS m/z 432 (MH$^+$). $^1$H NMR (CDCl$_3$) δ: 1.84 (2H, m), 3.41 (2H, m), 3.48 (3H, s), 3.55 (2H, m), 3.99 (3H, s), 6.4–8.4 (2H, b), 6.42 (1H, t), 6.90 (1H, bm), 7.05 (1H, s), 7.35 (2H, m), 7.52 (3H, m), 8.16 (2H, bs). Found: C,57.75; H,5.70; N,20.04; $C_{23}H_{25}N_7O_2$ 0.75.$CH_2Cl_2$ requires C,57.59; H,5.39; N,19.80%.

EXAMPLE 36

4-Amino-6,7-dimethoxy-5-phenyl-2-[3-(2-pyridyl) ethaneamino]quinazoline

The title compound was prepared by the method of Example 16(h) from the compound of Example 16(g) and 5 mole equivalents of 2-(2-aminoethyl)pyridine in the presence of catalytic potassium iodide. The product was purified by silica gel chromatography, eluting with ($CH_2Cl_2$/MeOH/ 0.88$NH_3$ 90/10/1, v/v) followed by trituration with ether to afford the title compound (31%) as a colourless foam. $R_f$ 0.27 ($CH_2Cl_2$/MeOH/0.88$NH_3$ 90/10/1, v/v). MS m/z 402 (MH$^+$). 3H NMR (CDCl$_3$) δ: 3.09 (2H, t), 3.45 (3H, s), 3.84 (2H, q), 4.00 (3H, s), 5.00 (2H, bs), 6.00–6.60 (1H, b), 6.99 (1H, s), 7.05 (1H, dd), 7.40 (1H, d), 7.35 (2H, m), 7.50 (3H, m), 7.59 (1H, t), 8.55 (1H, d). Found: C,63.48; H,5.84; N,15.77; $C_{23}H_{23}N_5O_2$0.5.$CH_2Cl_2$ requires C,63.57; H,5.45; N,15.78%.

EXAMPLE 37

4-Amino-2-[4-(furan-2-carbonyl)-1,4-piperazin-1-yl]-6,7-dimethoxy-5-phenylquinazoline The title compound was prepared by the method of Example 5(e) from the compound of Example 19(a) and furan-2-carboxylic acid. The product was purified by chromatography on silica gel, eluting with ($CH_2Cl_2$/MeOH/ 0.88$NH_3$ 90/10/1, v/v) followed by trituration with ether to give the title compound (66%) as a foam. $R_f$ 0.67 ($CH_2Cl_2$/ MeOH/0.88$NH_3$ 90/10/1, v/v). MS m/z 460 (MH$^+$). $^1$H NMR (CDCl$_3$) δ: 3.50 (3H, s), 3.74 (2H, m), 3.80–4.05 (6H, m), 3.97 (3H, s), 4.66 (2H, bs), 6.48 (1H, bs), 7.00 (2H, m), 7.39 (2H, m), 7.50 (4H, m). Found: C,65.71; H,6.42; N,14.80; $C_{25}H_{25}N_5O_4$ 0.5.ether requires C,65.30; H,6.09; N,14.11%.

EXAMPLE 38

(R/S)-4-Amino-6,7-dimethoxy-5-phenyl-2-[4-(tetrahydrofuran-2-carbonyl)-1,4-piperazin-1-yl] quinazoline The title compound was prepared by the method of Example 5(e) from the compound of Example 19(a) and (R/S)-tetrahydrofuran-2-carboxylic acid. The product was purified by chromatography on silica gel, eluting with ($CH_2Cl_2$/MeOH/0.88$NH_3$ 90/10/1, v/v) followed by trituration with ether to give the title compound (52%) as a foam. $R_f$ 0.58 ($CH_2Cl_2$/MeOH/0.88$NH_3$ 90/10/1, v/v). MS m/z 464 ($MH^+$). $^1$H NMR ($CDCl_3$) δ: 1.81–2.16 (4H, m), 3.09–4.08 (10H, m), 3.50 (3H, s), 4.00 (3H, s), 4.61 (3H, bm), 6.97 (1H, s), 7.37 (2H, m), 7.50 (3H, m). Found: C,63.14; H,6.52; N,14.00; $C_{25}H_{29}N_5O_4$ 0.2.$CH_2Cl_2$ 0.3.ether requires C,63.07; H,6.53; N,13.88%.

EXAMPLE 39

(R/S)-4-Amino-6,7-dimethoxy-5-phenyl-2-[4-(tetrahydropyran-2-carbonyl)-1,4-piperazin-1-yl]quinazoline The title compound was prepared by the method of Example 5(e) from the compound of Example 19(a) and (R/S)-tetrahydropyran-2-carboxylic acid [Nelson et al J. Org. Chem. 21, 798 (1956)]. The product was purified by chromatography on silica gel, eluting with ($CH_2Cl_2$/MeOH/0.88$NH_3$ 90/10/1, v/v) followed by trituration with ether to give the title compound (59%) as a solid. $R_f$ 0.48 ($CH_2Cl_2$/MeOH/0.88$NH_3$ 90/10/1, v/v). MS m/z 478 ($MH^+$). $^1$H NMR ($CDCl_3$) δ:1.44–2.02 (6H, m), 3.40–4.16 (10H, m), 3.50 (3H, s), 3.98 (3H, s), 4.11 (1H, dd), 4.60 (2H, bm), 6.94 (1H, s), 7.38 (2H, m), 7.50 (3H, m). Found: C,64.43; H,6.45; N,13.85; $C_{26}H_{31}N_5O_4$ 0.1.$CH_2Cl_2$ 0.3.ether requires C,64.51; H,6.82; N,13.71%.

EXAMPLE 40

4-Amino-6,7-dimethoxy-2-[4-(morpholinecarbonyl)-1,4-piperazin-1-yl]-5-phenylquinazoline Morpholinecarbonyl chloride (0.07 ml, 0.66 mmol) was added to a stirred solution of the compound of Example 19(a) (220 mg, 0.60 mmol) and 4-methylmorpholine (0.08 ml, 0.72 mmol) in $CH_2Cl_2$ (5 ml) at 0° C. under $N_2$. The reaction was stirred for 18 h, after which it was washed with $H_2O$, extracted with $CH_2Cl_2$, washed with saturated brine and the organic layer dried over $MgSO_4$ and evaporated. The product was purified on silica gel, eluting with ($CH_2Cl_2$/MeOH/0.88$NH_3$ 90/10/1, v/v) followed by trituration with ether to afford the tide compound as a solid (230 mg, 70%). $R_f$ 0.45 ($CH_2Cl_2$/MeOH/0.88$NH_3$ 90/10/1, v/v). MS m/z 479 ($MH^+$). $^1$H NMR ($CDCl_3$) δ: 3.30 (12H, m), 3.50 (3H, s), 3.84 (4H, m), 3.98 (3H, s), 4.60 (2H, bm), 6.97 (1H, s), 7.38 (2H, m), 7.48 (3H, m). Found: C,60.33; H,6.24; N,15.43; $C_{25}H_{30}N_6O_4$ 0.3.$CH_2Cl_2$ 0.5.ether requires C,60.35; H,6.61; N,15.46%.

EXAMPLE 41

4-Amino-6,7-dimethoxy-5-phenyl-2-[4-(thiomorpholine-1,1-dioxide-4-carbonyl)-1,4-diazepan-1-yl]quinazoline (a) Thiomorpholine-1,1-dioxide hydrochloride 2-Chloroethyl chloroformate (0.72 ml, 6.7 mmol) was added dropwise to a solution of 4-methylthiomorpholine-1,1-dioxide (11.0 g, 6.7 mmol) in toluene (10 ml) at 0° C. under $N_2$. After 10 min, the reaction was warmed and maintained at reflux for 2 h. On cooling, the reaction mixture was evaporated, partitioned between EtOAc and $H_2O$, the organic layer separated and washed sequentially with dilute HCl and saturated brine, the organic layer dried over $Na_2SO_4$ and evaporated. The residue was taken up in MeOH (10 ml) and heated at reflux for 2 h, after which time the reaction mixture was evaporated and triturated with EtOAc to afford the subtitle compound (415 mg, 36%) as a solid. $R_f$ 0.34 ($CH_2Cl_2$/MeOH/0.88$NH_3$ 90/10/1, v/v). MS m/z 136 ($MH^+$).

(b) 4-Amino-6,7-dimethoxy-5-phenyl-2-[4-(thiomorpholine-1,1-dioxide-4-carbonyl)-1,4-diazepan-1-yl]quinazoline The tide compound was prepared by the method of Example 18 using the product of step (a) in place of azetidinol. The product was purified by chromatography on silica gel, eluting with ($CH_2Cl_2$/MeOH(0.88$NH_3$ 90/10/1, v/v) followed by trituration with ether to give the title compound (25%) as a foam. $R_f$ 0.58 ($CH_2Cl_2$/MeOH/0.88$NH_3$ 90/10/1, v/v). MS m/z 541 ($MH^+$). $^1$H NMR ($CDCl_3$) δ: 1.97 (2H, m), 3.00 (4H, m), 3.40 (2H, m), 3.50 (3H, s), 3.55–3.73 (6H, m), 3.84 (2H, m), 3.904.06 (2H, m), 3.98 (3H, s), 4.59 (2H, bm), 6.90 (1H, s), 7.38 (2H, m), 7.50 (3H, m). Found: C,55.90; H,5.82; N,14.35; $C_{26}H_{32}N_6O_5S$ 0.3.$CH_2Cl_2$ 0.2.ether requires C,55.82; H,5.98; N,14.40%.

EXAMPLE 42

(R/S)-4-Amino-6,7-dimethoxy-5-phenyl-2-[tetrahydropyran-2-carbonyl)-1,4-diazepan-1-yl]quinazoline (a) (R/S)-1-(t-Butyloxycarbonyl)-4-(tetrahydropyran-2-carbonyl)-1,4-diazepane The subtitle compound was prepared by the method of Example 5(e) with Intermediate 1 and (R/S)-tetrahydropyran-2-carboxylic acid. The subtitle compound (73%) was obtained as a solid. $R_f$ 0.67 ($CH_2Cl_2$). MS m/z 312 ($MH^+$).

(b) (R/S)-1-(Tetrahydropyran-2-carbonyl)-1,4-diazepane hydrochloride

The subtitle compound was prepared by the method of Intermediate 3 from the product of step (a). The subtitle compound was obtained in quantitative yield as a hygroscopic solid. MS m/z 213 ($MH^+$).

(c) (R/S)-4-Amino-6,7-dimethoxy-5-phenyl-2-[4-(tetrahydropyran-2-carbonyl)-1,4-diazepan-1-yl]quinazoline The title compound was prepared by the method of 16(h) from the product of step (b) and the compound of Example 16(g). The product was purified by chromatography on silica gel, eluting with ($CH_2Cl_2$/MeOH(0.88$NH_3$ 90/10/1, v/v) followed by trituration with ether to afford the title compound (43%) as a foam. $R_f$ 0.61 ($CH_2Cl_2$/MeOH/0.88$NH_3$ 90/10/1, v/v). MS m/z 492 ($MH^+$). $^1$H NMR ($CDCl_3$) δ: 1.06–2.16 (8H, m), 3.16–4.40 (11H, m), 3.47 (3H, s), 3.98 (3H, s), 4.59 (2H, bm), 6.95 (1H, bs), 7.38 (2H, m), 7.50 (3H, m). Found: C,65.60; H,7.20; N,12.32; $C_{27}H_{33}N_5O_4$ 0.8.ether requires C,65.84; H,7.50; N,12.71%.

EXAMPLE 43

(S)-4-Amino-6,7-dimethoxy-2-[2-(morpholinecarbonyl)pyrrolidin-1-yl]-5-phenylquinazoline The title compound was prepared by the method of 16(h) from (S)-proline morpholine amide [prepared according to the method of Asami, Bull. Chem. Soc. Jpn., 63, 721 (1990), replacing Cbz-(S)-proline with tBoc-(S)proline) and the compound of Example 16(g). The product was purified by chromatography on silica gel, eluting with ($CH_2Cl_2$/MeOH/0.88$NH_3$ 90/10/1, v/v) followed by trituration with ether to afford the title compound (53%) as a foam. $R_f$ 0.39 ($CH_2Cl_2$/MeOH/0.88$NH_3$ 90/10/1, v/v). MS m/z 464 ($MH^+$). $^1$H NMR (CDCl$_3$) δ: 1.99 (2H, m), 2.02 (2H, m), 3.48 (3H, s), 3.60 (6H, m), 3.84 (4H, m), 3.97 (3H, s), 4.58 (2H, bm), 5.02 (1H, bs), 6.95 (1H, bs), 7.35 (2H, m), 7.47 (3H, m). Found: C,63.68; H,6.54; N,13.92; C$_{25}$H$_{29}$N$_5$O$_4$ 0.5.ether 0.1.CH$_2$Cl$_2$ requires C,63.72; H,6.75; N,13.70%.

EXAMPLE 44

4-Amino-6,7-dimethoxy-5-phenyl-2-(5,6,7,8-tetrahydro-1,6-naphthyrid-6-yl)quinazoline The title compound was prepared by the method of 16(h) from 5,6,7,8-tetrahydro-1,6-naphthyridine [Shiozawa et al. Chem. Pharm. Bull., U, 2522 (1984)) and the compound of Example 16(g). The product was purified by chromatography on silica gel, eluting with (CH$_2$Cl$_2$/MeOH/0.88NH$_3$ 93/7/1, v/v) followed by trituration with ether to afford the title compound (33%) as a foam. R$_f$ 0.50 (CH$_2$Cl$_2$/MeOH/0.88NH$_3$ 90/10/1, v/v). MS m/z 492 (MH$^+$). $^1$H NMR (CDCl$_3$) δ: 3.10 (2H, t), 3.48 (3H, s), 3.98 (3H, s), 4.18 (2H, t), 4.66 (2H, bs), 5.00 (2H, s), 7.01 (1H, s), 7.13 (1H, dd), 7.39 (2H, m), 7.50 (4H, m), 8.42 (1H, d). Found: C,68.05; H,5.80; N,15.89; C$_{25}$H$_{23}$N$_5$O$_2$ 0.1.CH$_2$Cl$_2$ 0.4.ether requires C,68.35; H,6.07; N,15.51%.

EXAMPLE 45

4-Amino-6,7-dimethoxy-5-phenyl-2-(5,6,7,8-tetrahydro-1,3,6-triazanaphth-6-yl)quinazoline (a) 1-(t-Butyloxycarbonyl)-3-(N,N-dimethylmethylidene)-4-piperidone Dimethylformamide dimethyl acetal (5.82 ml, 0.044 mol) was added to a stirred solution of 1-Boc4-piperidone [Ashwood et al J. Chem. Soc., Perkin 1, 641 (1995)] (8.73 g, 0.044 mol) in DMF (80 ml) and the reaction mixture was heated to 80° C. under N$_2$ for 18 h. After cooling, the DMF was removed under reduced pressure and the residue was partitioned between EtOAc and H$_2$O, the organic layer washed with H$_2$O and saturated brine, then dried over MgSO$_4$ and evaporated to afford the subtitle compound as a solid (8.44 g, 76%). R$_f$ 0.33 (CH$_2$Cl$_2$/MeOH/0.88NH$_3$ 90/10/1, v/v). MS m/z 255 (MH$^+$).

(b) 6-(t-Butyloxycarbonyl)-(5,6,7,8-tetrahydro-1,3,6-triazanaphthalene)

Sodium (762 mg, 0.033 mol) was added to EtOH (150 ml) followed by formamidine acetate (3.45 g, 0.033 mol) and the reaction was stirred at room temperature under N$_2$ for 30 min. A solution of the product of step (a) (8.43 g, 0.033M) in EtOH(50 ml) was then added and the reaction heated to reflux for 18 h after which time the mixture was cooled and concentrated under reduced pressure. The residue was partitioned between EtOAc and H$_2$O, the organic layer washed with saturated brine and dried over MgSO$_4$. Purification on silica gel, eluting with CH$_2$Cl$_2$/MeOH (96/4, v/v) afforded the subtitle compound as an oil (5.09 g, 65%). R$_f$ 0.57 (CH$_2$Cl$_2$/MeOH/0.88NH$_3$ 90/10/1, v/v). MS m/z 236 (MH$^+$).

(c) 5,6,7,8-Tetrahydro-1,3,6-triazanaphthalene

HCl was bubbled through a solution of the product of step (b) (4.80 g, 0.020 mol) in a mixture of MeOH and ether (50 ml, 1/1, v/v) at 0° C. until saturated. The mixture was then allowed to reach room temperature over 2 h, after which time a precipitate formed. This was isolated by decanting off the supernatant solution, washing with ether (2×) and drying in vacuo to afford the subtitle compound as a colourless solid (2.85 g, 81%). R$_f$ 0.13 (CH$_2$Cl$_2$/MeOH/0.88NH$_3$ 90/10/1, v/v). MS m/z 136 (MH$^+$).

(d) 4-Amino-6,7-dimethoxy-5-phenyl-2-(5,6,7,8-tetrahydro-1,3,6-triazanaphth-6-yl)quinazoline The title compound was prepared by the method of 16(h) from the product of step (c) and the compound of Example 16(g). The product was purified by chromatography on silica gel, eluting with (EtOAc/hexane 7/1, v/v) followed by trituration with ether to afford the title compound (42%) as a light yellow foam. R$_f$ 0.48 (CH$_2$Cl$_2$/MeOH/0.88NH$_3$ 90/10/1, v/v). MS m/z 415 (MH$^+$). $^1$H NMR (CDCl$_3$) δ: 3.03 (2H, t), 3.50 (3H, s), 4.00 (3H, s), 4.21 (2H, t), 4.68 (2H, bs), 5.00 (2H, s), 7.00 (1H, s), 7.37 (2H, m), 7.50 (3H, m), 8.55 (1H, s), 8.99 (1H, s). Found: C,65.77; H,5.48; N,19.31; C$_{23}$H$_{22}$N$_6$O$_2$ 0.2.ether 0.25.H$_2$O requires C,65.90; H,5.69; N,19.37%.

EXAMPLE 46

4-Amino-6,7-dimethoxy-2-[(4-methanesulfonamido)isoindolin-2-yl]-5-phenylquinazline (a) 4-Methanesulfonamidophthalimide Methanesulfonylchloride (2.6 ml, 0.034 mol) was added dropwise to a stirred suspension of 4-aminophthalimide (5.0 g, 0.031 mol) in pyridine (50 ml). The mixture was stirred for 48 h under N$_2$ at room temperature, after which time the solid formed was isolated by filtration, washing well with H$_2$O and CH$_2$Cl$_2$ and then dried in vacuo to afford the subtitle compound as a colourless solid (5.67 g, 76%). R$_f$ 0.52 (CH$_2$Cl$_2$/MeOH/0.88NH$_3$ 90/10/1, v/v). MS m/z 241 (MH$^+$).

(b) 4-(Methanesulfonamido)isoindoline hydrochloride

Borane.THF complex (1M solution in THF, 106 ml, 0.11 mol) was added dropwise to a stirred suspension of the product of step (a) in THF (100 ml) and the reaction heated to reflux for 18 h. The reaction mixture was then cooled to 0° C. and MeOH (50 ml) was added cautiously, followed by 6N HCl (70 ml). The mixture was then extracted with CH$_2$Cl$_2$ (3×) and the aqueous layer evaporated to dryness. The residue was taken up into CH$_2$Cl$_2$/MeOH (95/5, v/v) and the inorganic solid filtered off. The filtrate was concentrated to give a solid which was triturated with CH$_2$Cl$_2$ and dried in vacuo to afford the subtitle compound as a colourless solid (2.67 g, 46%). R$_f$ 0.09 (CH$_2$Cl$_2$/MeOH/0.88NH$_3$ 90/10/1, v/v). MS m/z 213 (MH$^+$).

(c) 4-Amino-6,7-dimethoxy-2-[(4-methanesulfonamido)isoindolin-2-yl]-5-phenylquinazoline The title compound was prepared by the method of 16(h) from the product of step (b) and the compound of Example 16(g). The product was purified by chromatography on silica gel, eluting with (EtOAc/hexane 7/1, v/v) followed by trituration with ether to afford the title compound (41%) as a solid. R$_f$ 0.52 (CH$_2$Cl$_2$/MeOH/0.88NH$_3$ 90/10/1, v/v). MS m/z 492 (MH$^+$). $^1$H NMR (CDCl$_3$) δ: 3.03 (3H, s), 3.50 (3H, s), 4.00 (3H, s), 4.71 (2H, bs), 4.90 (4H, bs), 7.03 (1H, s), 7.13 (1H, d), 7.21 (1H, s), 7.30 (1H, d), 7.40 (2H, m), 7.52 (4H, m). Found: C,59.87; H,5.51; N,12.72; C$_{25}$H$_{25}$N$_5$O$_4$S 0.8.EtOAc requires C,60.26; H,5.63; N,12.46%.

EXAMPLE 47

(S)-4-Amino-6,7-dimethoxy-2-[3-(morpholinecarbonyl)pyrrolidin-1-yl]-5-phenylquinazoline (a) (R/S)-1-(t-Butyloxycarbonyl)-3-(morpholinecarbonyl)pyrrolidine The subtitle compound was prepared by the method of Example 5(e) with (R/S)-1-Boc-pyrrolidine-3-carboxylic acid (MacLeod et al J. Med. Chem., 33, 2052 (1990)] and morpholine. The subtitle compound (62%) was obtained as an oil. R$_f$ 0.69 (CH$_2$Cl$_2$/MeOH 95/5, v/v). MS m/z 285 (MH$^+$).

(b) (R/S)-3-(Morpholinecarbonyl)pyrrolidine, hydrochloride

The subtitle compound was prepared by the method of Example 45(c). The subtitle compound (64%) was obtained as a colourless solid. $R_f$ 0.07 ($CH_2Cl_2$/MeOH/0.88$NH_3$ 90/10/1, v/v). MS m/z 185 ($MH^+$).

(c) (S)-4-Amino-6,7-dimethoxy-2-[3-(morpholinecarbonyl)pyrrolidin-1-yl]-5-phenylquinazoline The title compound was prepared by the method of 16(h) from the product of step (b) and the compound of Example 16(g). The product was purified by chromatography on silica gel, eluting with ($CH_2Cl_2$/MeOH/$NH_3$ 90/10/1, v/v) followed by trituration with ether to afford the title compound (41%) as a solid. $R_f$ 0.52 ($CH_2Cl_2$/MeOH/0.88$NH_3$ 90/10/1, v/v). MS m/z 464 ($MH^+$). $^1H$ NMR ($CDCl_3$) δ: 2.13 (1H, m), 2.35 (1H, m), 3.26(1H, m), 3.47 (3H, s), 3.52–3.76 (10H, m), 3.84 (1H, m), 3.98 (3H, s), 4.00 (1H, m), 4.70 (2H, bs), 7.05 (1H, s), 7.38 (2H, m), 7.45 (3H, m). Found: C,62.55; H,6.28; N,14.27; $C_{21}H_{29}N_5O_4$ 0.25. $CH_2Cl_2$ requires C,62.55; H,6.13; N,14.45%.

EXAMPLE 48

4-Amino-6,7-dimethoxy-5-(2-methoxyphenyl)-2-(5,6,7,8-tetrahydro-1,6-naphthyrid-6-yl)quinazoline (a) 4-Amino-6,7-dimethoxy-5-iodo-2-(5,6,7,8-tetrahydro-1,6-naphthyrid-6-yl)quinazoline The subtitle compound was prepared by the method of 16(h) from 1,2,3,4-tetrahydro-1,6-naphthyridine and the compound of Example 20(b).The subtitle compound was obtained in quantitative yield as a brown foam. $R_f$ 0.35 ($CH_2Cl_2$/MeOH/0.88$NH_3$ 90/10/1, v/v). MS m/z 464 ($MH^+$).

(b) 4-Amino-6,7-dimethoxy-5-(2-methoxyphenyl)-2-(5,6,7,8-tetrahydro-1,6-naphthyrid-6-yl)quinazoline The title compound was prepared by the method of Example 1(a) with 2-methoxyphenylboronic acid and the product of step (a). The product was purified by trituration with EtOAc/hexane to afford the title compound (18%) as an off-white solid. $R_f$ 0.33 ($CH_2Cl_2$/MeOH/0.88$NH_3$ 90/10/1, v/v). MS m/z 444 ($MH^+$). $^1H$ NMR ($D_6$-DMSO) δ: 3.06 (2H, m), 3.50 (3H, s), 3.74 (3H, s), 4.00 (3H, s), 4.21 (2H, m), 4.74 (2H, s), 4.99 (2H, s), 6.90–7.16 (4H, m), 7.22 (1H, d), 7.39–7.55 (2H, m), 8.40 (1H, d). Found: C,66.52; H,5.84; N,14.83; $C_{25}H_{75}N_5O_3$ 0.5.$H_2O$ 0.1.hexane requires C,66.67; H,5.73; N,15.20%.

EXAMPLE 49

4-Amino-11-methoxy-2-[4-(4-morpholinecarbonyl)-1,4-diazepan-1-yl]-9H-[2]benzopyrano-[3,4-c]quinazoline (a) 3-Benzyloxy-4-methoxybenzonitrile 3-Benzyloxy-4-methoxybenzaldehyde (50 g, 0.21 mol) was added to a solution of sodium acetate (33.9 g, 0.41 mol) and hydroxylamine hydrochloride (28.73 g, 0.41 mol) in acetic acid (200 ml) and the resulting suspension was heated to reflux for 18 h. After cooling, the reaction mixture was partitioned between $CH_2Cl_2$ and $H_2O$ and the aqueous phase was further extracted with $CH_2Cl_2$. The combined organic layers were dried over $MgSO_4$ and evaporated to afford the subtitle compound as a buff-coloured solid (43.9 g, 89%). $R_f$ 0.70 (toluene/EtOAc 4/1, v/v).

(b) 5-Benzyloxy-4-methoxy-2-nitro-benzonitrile

A solution of the product of step (a) (43.8 g, 0.18 mol) in glacial acetic acid (87 ml) was added dropwise to concentrated nitric acid (70% w/w, 244 ml) with periodic cooling to maintain the reaction temperature below 30° C. Once the addition was complete, the reaction was stirred for a further 30 min, after which time the mixture was poured into $H_2O$ (1 L) and stirred for 30 min. The resulting precipitate was isolated by filtration, washing with $H_2O$ followed by drying in vacuo at 50° C. to afford the subtitle compound as a white solid (35.1 g, 68%). $R_f$ 0.70 (EtOAc/hexane 1/1, v/v).

(c) 2-Amino-5-benzyloxy-4-methoxybenzonitrile

To a solution of the product of step (b) (35.0 g, 0.12 mol) in $CH_2Cl_2$ (500 ml) was added tetra-n-butylammonium chloride (20.3 g, 0.074 mol) followed by a solution of sodium dithionite hydrate (118.0 g, 0.61 mol) in $H_2O$ (400 ml) and the mixture was stirred vigorously for 2 h at room temperature. A further quantity of sodium dithionite hydrate (47.2 g) was then added and stirring continued for 1 h. The reaction mixture was then basified with 2N aqueous NaOH and the phases separated. The aqueous layer was extracted twice more with $CH_2Cl_2$ and the combined organic layers dried over $MgSO_4$ and concentrated in vacuo to a volume of 60 ml. Treatment with excess ethereal HCl led to the precipitation of an orange solid which was washed with ether and then dissolved in a mixture of $CH_2Cl_2$ and 2N aqueous NaOH. The phases were separated and the organic layer concentrated in vacuo and then dissolved in EtOAc and passed through a 5 cm plug of silica gel, eluting with EtOAc. On evaporation and drying in vacuo, the subtitle compound was obtained as a yellow solid (26.7 g, 85%). $R_f$ 0.76 ($CH_2Cl_2$/MeOH/0.88$NH_3$ 90/10/1, v/v). MS m/z 255 ($MH^+$).

(d) 4-Amino-6-benzyloxy-2-hydroxy-7-methoxyquinazoline

A solution of the product of step (c) (26.7 g, 0.10 mol) in $CH_2Cl_2$ was treated with sodium cyanate (17.1 g, 0.26 mol) and trifluoroacetic acid (20.9 ml, 0.26 mol) was added dropwise to the resulting mixture at room temperature. After 45 min, the mixture was diluted with $CH_2Cl_2$ (1L) and stirred for a further 18 h. The mixture was then concentrated in vacuo and partitioned between MeOH and 2N aqueous NaOH and stirred for 2 h. The MeOH was then removed in vacuo and the yellow solid isolated by filtration, washing sequentially with $H_2O$, acetone and ether to afford the subtitle compound as a yellow solid (18.0 g, 54%). A further quantity of product was obtained by concentration of the filtrate, acidification with concentrated HCl (95 ml), warming on a steam bath for 5 min, cooling and neutralisation with solid potassium carbonate. The solid obtained was isolated by filtration, washing sequentially with $H_2O$, EtOH and ether to afford the subtitle compound as a yellow solid (12.11 g, 93% combined yield). $R_f$ 0.23 ($CH_2Cl_2$/MeOH/0.88$NH_3$ 84/14/2, v/v). MS m/z 298 ($MH^+$).

(e) 4-Amino-6-benzyloxy-2-chloro-7-methoxyquinazoline

DMF (7.9 ml, 0.10 mol) was added dropwise to $POCl_3$ with stirring. After 10 min, the product of step (d) was added portionwise and the resulting mixture heated at 90° C. for 1.5 h, then cooled and poured into EtOAc (750 ml). The mixture was neutralised by the portionwise addition of aqueous sodium carbonate and the phases were separated. The organic layer was evaporated to dryness and the residue combined with the organic phase which was then treated with aqueous NaOH to basify (pH 10) and the mixture was heated at 90° C. for 2 h. After cooling, the mixture was partitioned between $CH_2Cl_2$ (1 L) and $H_2O$ (1 L), the organic phase washed with $H_2O$, dried over $MgSO_4$ and evaporated to give a pale yellow solid. Trituration with isopropanol afforded the subtitle compound as a colourless solid (4.64 g, 29%). $R_f$ 0.64 (EtOAc/MeOH 95/5, v/v). MS m/z 316, 318 ($MH^+$).

(f) 2-Amino-6-benzyloxy-7-methoxy-2-[4-(4-morpholinecarbonyl)-1,4-diazepan-1-yl]

The subtitle compound was prepared by the method of 16(h) from the product of step (e) and the compound of Example 16(g). The product was purified on silica gel eluting with EtOAc/MeOH (9/1, v/v) to afford the subtitle compound (46%) as a foam. $R_f$ 0.67 ($CH_2Cl_2$/MeOH/0.88$NH_3$ 84/14/2, v/v). MS m/z 493 (MI).

(g) 2-Amino-6-hydroxy-7-methoxy-2-[4(4-morpholinecarbonyl)-1,4-diazepan-1-yl]

The product of step (f) (360 mg, 0.73 mmol) was dissolved in EtOH (60 ml), 10% palladium on charcoal (100 mg, 0.09 mmol) was added and the reaction mixture hydrogenated at room temperature at a pressure of 414 kPa (60 psi). for 18 h. The reaction mixture was filtered and concentrated in vacuo and the residue purified on silica gel, eluting with $CH_2Cl_2$/MeOH/0.88$NH_3$ (92/7/1, v/v) to afford the subtitle compound as a foam (135 mg, 47%). $R_f$ 0.33 ($CH_2Cl_2$/MeOH/0.88$NH_3$ 84/14/2, v/v). MS m/z 403 ($MH^+$).

(h) 2Amino-6-(o-bromobenzyloxy)-7-methoxy-2-4-(4-morpholinecarbonyl)-1,4-diazepan-1-yl]

Sodium hydride (60% dispersion in mineral oil, 1001 mg, 2.5 mmol) was added to DMF (20 ml) and this was followed by the addition of the product of step (g) (1.0 g, 2.5 mmol) and the reaction was stirred at room temperature for 20 min. o-Bromobenzyl bromide (625 mg, 2.5 mmol) was then added to the reaction which was left to stir for 1 h, after which time it was quenched with $H_2O$, extracted with EtOAc (2×), the combined organic layers washed with $H_2O$, dried over $MgSO_4$ and evaporated to afford the product as a foam (1.2 g, 84%). $R_f$ 0.48 ($CH_2Cl_2$/MeOH/0.88$NH_3$ 84/14/2, v/v). MS m/z 571, 573 ($MH^+$).

(i) Amino-11-methoxy-2-[4-(4-morpholinecarbonyl)-1,4-diazepan-1-yl]-9H-[2]benzopyrano-[3,4-c] quinazoline To a solution of the product of step (i) (1.2 g, 2.0 mmol) in DMA (10 ml) was added sodium carbonate (254 mg, 2.4 mmol) and palladium acetate (45 mg, 0.2 mmol) and the reaction mixture was heated to 130° C. for 48 h under $N_2$. The reaction mixture was then cooled partitioned between EtOAc and $H_2O$ and the organic layer dried over $MgSO_4$ and evaporated. The product was purified by chromatography on silica gel eluting with $CH_2Cl_2$/MeOH/0.88$NH_3$ (95/5/0.5, v/v) followed by trituration with hexane to afford the title compound as a light yellow solid (114 mg, 12%). $R_f$ 0.76 ($CH_2Cl_2$/MeOH/0.88$NH_3$ 84/14/2, v/v). MS m/z 491 ($MH^+$). $^1H$ NMR ($CDCl_3$) δ: 2.06 (2H, m), 3.18 (4H, m), 3.42 (2H, m), 3.60 (2H, m), 3.68 (4H, m), 3.94 (2H, m), 4.00 (5H, m), 4.90 (2H, bs), 5.09 (2H, s), 6.87 (1H, s), 7.21–7.52 (4H, m). Found: C,62.18; H,6.34; N,14.66; $C_{26}H_{30}N_6O_4$. 0.6.hexane 0.5. $CH_2Cl_2$ requires C,61.84; H,6.74; N,14.38%.

EXAMPLE 50

4-Amino-11-methoxy-2-[4(4-morpholinecarbonyl)-1,4-diazepan-1-yl]-9H-[2]benzopyrano-[3,4-c] quinoline (a) 3-(o-Bromobenzyloxy)-4-methoxybenzonitrile To a solution of 2-bromobenzyl alcohol (16.50 g, 88.2 mmol) in DMF (100 ml) was added sodium hydride (60% dispersion in mineral oil, 2.94 g, 73.5 mmol) and this was followed by 3-fluoro-4-methoxybenzonitrile (8.88 g, 58.8 mmol) and the resulting mixture was heated to 90° C. for 2 h under $N_2$. After cooling, the mixture was partitioned between ether and $H_2O$, the organic layer washed sequentially with 0.5 N HCl and saturated brine and then dried over $MgSO_4$. Trituration with ether/pentane (1/3, v/v) afforded the subtitle compound as an off-white solid (13.35 g, 71%). $R_f$ 0.27 (hexane/EtOAc 5/1, v/v). MS m/z 318, 320 ($MH^+$).

(b) 1-Cyan-6H-dibenzo[b,d]pyran

The subtitle compound was prepared by the method of Example 49(i) from the product of step (a). The product was purified by chromatography on silica gel, eluting with hexane/EtOAc (4/1, v/v) followed by trituration with hexane/EtOAc (4/1, v/v) to afford the subtitle compound (41%) as a colourless solid. $R_f$ 0.16 (hexane/EtOAc, 4/1, v/v). MS m/z 238 ($MH^+$).

(c) 1-Cyano-2-nitro-6H-dibenzo[b,d]pyran

The subtitle compound was prepared by the method of Example 16(a) from the product of step (b). The product was purified by chromatography on silica gel, eluting with $CH_2Cl_2$ to afford the subtitle compound (42%) as a pale yellow solid. $R_f$ 0.26 (hexane/$CH_2Cl_2$ 1/2, v/v). MS m/z 283 ($MH^+$).

(d) 2-Amino-1-cyano-6H-dibenzo[b,d]pyran

The subtitle compound was prepared by the method of Example 49(c) from the product of step (c). The product was purified by chromatography on silica gel, eluting with $CH_2Cl_2$/MeOH (98/2, v/v) to afford the subtitle compound (85%) as a yellow solid. $R_f$ 0.81 ($CH_2Cl_2$/MeOH/0.88$NH_3$ 93/7/1, v/v). MS m/z 253 ($MH^+$).

(e) 1-Cyano-2-{1-[4-(morpholine-4-carbonyl)-1,4-diazepan-1-yl]ethylideneamino}-6H-dibenzo[b,d]pyran The subtitle compound was prepared by the method of Example 1(c) from the product of step (d) and Intermediate 4. The product was purified by chromatography on silica gel, eluting with $CH_2Cl_2$/MeOH (97/3, v/v) to afford the subtitle compound (97%) as a yellow foam. $R_f$ 0.56 ($CH_2Cl_2$/MeOH/0.88$NH_3$ 93/7/1, v/v). MS m/z 490 ($MH^+$).

(f) 4-Amino-11-methoxy-2-[4-(4-morpholinecarbonyl)-1,4-diazepan-1-yl]-9H-[2]benzopyrano-[3,4-c]quinoline The title compound was prepared by the method of Example 1 (d) from the product of step (e). The product was purified by chromatography on silica gel, eluting with $CH_2Cl_2$/MeOH (9/1, v/v) followed by dissolution in $CH_2Cl_2$ and precipitation with toluene to afford the subtitle compound (40%) as a yellow solid. $R_f$ 0.35 ($CH_2Cl_2$/MeOH/0.88$NH_3$ 93/7/1, v/v). MS m/z 490 ($MH^+$). $^1H$ NMR ($CDCl_3$) δ: 2.10 (2H, m), 3.16 (4H, m), 3.40 (2H, m), 3.65 (6H, m), 3.77 (2H, m), 3.98 (2H, m), 4.01 (3H, s), 4.35 (2H, s), 4.90 (1H, d), 5.30 (1H, d), 5.94 (1H, s), 7.05 (1H, s), 7.21–7.52 (4H, m). Found: C,65.86; H,6.33, N,13.30; $C_{27}H_{31}N_5O_4$. 0.2.toluene 0.5.$H_2O$ requires C,65.98; H,6.55, N,13.55%.

EXAMPLE 51

4-Amino-7-methoxy-2-[4-(4-morpholinecarbonyl)-1,4-diazepan-1-yl]-5-phenyl-6-(2,2,2-trifluoroethoxy) quinoline (a) 4-Methoxy-3-(2,2,2-trifluoroethoxy)benzoic Acid, Methyl Ester To a mixture of isovanillic acid methyl ester (33.0 g, 0.18 mol) and potassium carbonate (41.4 g, 0.30 mol) in DMF (100 ml) was added a solution of trifluoroethyl triflate [Burdon et al Tetrahedron 21, 1 (1965)] (65.0 g, 0.28 mol) in $CH_2Cl_2$. The mixture was stirred at room temperature for 18 h then evaporated to 50 ml, the mixture partitioned between ether and $H_2O$, the organic layer washed with $H_2O$ and saturated brine, then dried over $MgSO_4$ and evaporated. The resulting solid was triturated with hexane to give the subtitle compound as an off-white solid (42.55 g, 90%). $R_f$ 0.47 ($CH_2Cl_2$). MS m/z 265 ($MH^+$).

(b) 4-Methoxy-3-(2,2,2-trifluoroethoxy)benzoic Acid

The product of step (a) (42.3 g, 0.16 mol) was dissolved in MeOH (500 ml) and 2N aqueous NaOH (160 ml, 0.32 mol) was added and the mixture stirred at room temperature for 3 h and then at 50° C. for 1 h. After cooling, the solution was concentrated in vacuo, treated with 2N HCl and extracted with EtOAc (3×). The combined organic extracts were dried over MgSO$_4$, filtered and evaporated to give the subtitle compound as a colourless solid (40.4 g, quantitative). R$_f$ 0.13 (hexane/EtOAc 1/1, v/v). MS m/z 251 (MH$^+$).

(c) 2-[4'-Methoxy-3'-(2,2,2-trifluoroethoxyphenyl)]-4,4-dimethyl-Δ$^2$-oxazoline The subtitle compound was prepared by the method of Example 3(a) from the product of step (b). The product was purified on silica gel, eluting with CH$_2$Cl$_2$/MeOH (95/5) to give the subtitle compound (80%) as a colourless solid. R$_f$ 0.54 (EtOAc). MS m/z 304 (MH$^+$).

(d) 2-[2'-Iodo-4'-methoxy-3'-(2,2,2-trifluoroethoxyphenyl)]-4,4-dimethyl-Δ$^2$-oxazoline The subtitle compound was prepared by the method of Example 3(b) from the product of step (c). The product was purified on silica gel, eluting with EtOAc/hexane (3/2, v/v) followed by trituration with ether/hexane (1/3, v/v) to give the subtitle compound (26%) as a colourless solid. R$_f$ 0.27 (EtOAc/hexane 1/1, v/v). MS m/z 430 (MH$^+$).

(e) 2-Iodo-4-methoxy-3-(2,2,2-trifluoroethoxy)benzonitrile

The subtitle compound was prepared by the method of Example 3(c) from the product of step (d). The product was triturated with ether/hexane (1/3, v/v) to give the subtitle compound (97%) as a colourless solid. R$_f$ 0.50 (EtOAc/hexane 1/1, v/v). MS m/z 358 (MH$^+$).

(f) 2-Iodo-4-methoxy-6-nitro-3-(2,2,2-trifluoroethoxy)benzonitrile

The subtitle compound was prepared by the method of Example 3(d) from the product of step (e). The product was triturated with ether to give the subtitle compound (61%) as a colourless solid. R$_f$ 0.25 (EtOAc/hexane 1/2, v/v). MS m/z 403 (MH$^+$).

(g) 2-Amino-6-iodo-4-methoxy-5-(2,2,2-trifluoroethoxy)benzonitrile

The subtitle compound was prepared by the method of Example 49(c) from the product of step (f). The subtitle compound (70%) was obtained as a colourless solid. R$_f$ 0.74 (CH$_2$Cl$_2$/MeOH/0.88NH$_3$ 93/7/1, v/v). MS m/z 373 (MH$^+$).

(h) 2-Iodo-4-methoxy-6-{1-[4-(morpholine-4-carbonyl)-1,4-diazepan-1-yl]ethylideneamino}-3-(2,2,2-trifluoroethoxy)benzonitrile The subtitle compound was prepared by the method of Example 1(c) from the product of step (g) and Intermediate 4. The product was purified by chromatography on silica gel eluting with CH$_2$Cl$_2$/MeOH (9/1, v/v) followed by crystallisation from EtOAc to give the subtitle compound (64%) as a colourless solid. R$_f$ 0.12 (EtOAc). MS m/z 610 (MH$^+$).

(i) 4-Amino-5-iodo-7-methoxy-2-[4-(4-morpholinecarbonyl)-1,4-diazepan-1-yl]-6-(2,2,2-trifluoroethoxy)quinoline The subtitle compound was prepared by the method of Example 1 (d) from the product of step (h). The product was purified by chromatography on silica gel eluting with CH$_2$Cl$_2$/MeOH (9/1, v/v) to give the subtitle compound (20%) as a colourless solid. R$_f$ 0.15 (CH$_2$Cl$_2$/MeOH 9/1, v/v). $^1$H NMR (CDCl$_3$) δ: 2.06 (2H, m), 3.16 (4H, m), 3.32 (2H, m), 3.58 (2H, m), 3.65 (4H, m), 3.70 (2H, m), 3.90 (2H, m), 3.97 (3H, s), 4.37 (2H, t), 5.55 (2H, bs), 5.90 (1H, s), 7.05 (1H, bs).

(j) 4-Amino-7-methoxy-2-[4-(4-morpholinecarbonyl)-1,4-diazepan-1-yl]-5-phenyl-6-(2,2,2-trifluoroethoxy)quinoline The subtitle compound was prepared by the method of Example 1(a) from the product of step (i) and phenylboronic acid. The product was purified by chromatography on silica gel eluting with CH$_2$Cl$_2$/MeOH (9/1, v/v) to give the subtitle compound (55%) as a foam. R$_f$ 0.12 (CH$_2$Cl$_2$/MeOH 9/1, v/v). MS m/z 560 (MH$^+$). $^1$H NMR (CDCl$_3$) δ: 2.06 (2H, m), 3.16 (4H, m), 3.35 (2H, m), 3.55–3.80 (8H, m), 3.82–4.13 (9H, m), 5.70 (1H, s), 7.65 (1H, bs), 7.37 (2H, m), 7.45 (3H, m).

EXAMPLE 52

2-Amino-6,7-dimethoxy-5-phenyl-2-(5,6,7,8-tetrahydro-1,3,7-triazanaphth-7-yl)quinazoline (a) 1-Trityl-3-piperidone Trityl chloride (13.1 g, 47.0 mmol) was added to a stirred suspension of 3-piperidone hydrochloride (5.79 g, 42.7 mmol) and triethylamine (14.9 ml, 107 mmol) in CH$_2$Cl$_2$ (100 ml) and the reaction was stirred for 16 h under N$_2$ at room temperature. The resulting mixture was filtered and the filtrate washed sequentially with H$_2$O and 5% aqueous citric acid, dried over MgSO$_4$ and evaporated under reduced pressure. Trituration with pentane afforded the subtitle compound as a colourless solid (4.8 g, 33%). R$_f$ 0.23 (CH$_2$Cl$_2$/pentane 2/3, v/v). $^1$H NMR (CDCl$_3$) δ: 2.05 (2H, m), 2.35 (2H, m), 2.45 (2H, m), 2.85 (2H, s), 7.06–7.55 (15H, m).

(b) 4-(N,N-Dimethylmethylidene)-1-trityl-3-piperidone

The subtitle compound was prepared by the method of Example 45(a) from the product of step (a). Crystallisation from ether afforded the subtitle compound (52%) as a colourless solid. R$_f$ 0.23 (CH$_2$Cl$_2$/pentane 2/3, v/v). $^1$H NMR (CDCl$_3$) δ: 2.35 (2H, t), 2.87 (2H, t), 2.97 (2H, s), 3.13 (6H, s), 7.13 (3H, m), 7.24 (7H, m), 7.50 (6H, m).

(c) 7-Trityl-(5,6,7,8-tetrahydro-1,3,7-triazanaphthalene)

The subtitle compound was prepared by the method of Example 45(b) from the product of step (b). The product was purified by chromatography on silica gel, eluting with CH$_2$Cl$_2$/ether (9/1, v/v) to afford the subtitle compound (51%). R$_f$ 0.33 (CH$_2$Cl$_2$/ether 85/15, v/v). $^1$H NMR (CDCl$_3$) δ: 2.60 (2H, t), 2.97 (2H, t), 3.58 (2H, s), 7.06–7.37 (8H, m), 7.52 (7H, m), 8.45 (1H, s), 8.90 (1H, s)

(d) 5,6,7,8-Tetrahydro-1,3,7-triazanaphthalene hydrochloride

The subtitle compound was prepared by the method of Example 45(c) from the product of step (c). The product crystallised from MeOH/ether to afford the subtitle compound (65%) as an orange hygroscopic solid. $^1$H NMR (d$_6$-DMSO) δ: 3.06 (2H, m), 3.40 (2H, m), 4.26 (2H, s), 8.68 (1H, s), 9.00 (1H, s), 9.96 (2H, bs).

(e) 2-Amino-6,7-dimethoxy-5-phenyl-2-(5,6,7,8-tetrahydro-1,3,7-triazanaphth-7-yl)quinazoline The title compound was prepared by the method of 16(h) from the product of step (d) and the compound of Example 16(g). The product was purified by chromatography on silica gel, eluting with CH$_2$Cl$_2$/MeOH (95/5, v/v) to afford the title compound (36%) as a foam. R$_f$ 0.16 (CH$_2$Cl$_2$/MeOH 95/5, v/v). MS m/z 415 (MH$^+$). $^1$H NMR (CDCl$_3$) δ: 2.90 (2H, m), 3.50 (3H, s), 4.00 (3H, s), 4.16 (2H, m), 4.65 (2H, bs), 5.05 (2H, s), 7.00 (1H, s), 7.38 (2H, m), 7.50 (3H, m), 8.50 (1H, s), 9.02 (1H, s). Found: C,63.56; H,5.20; N,18.97; C$_{23}$H$_{22}$N$_6$O$_2$ 0.3.CH$_2$Cl$_2$ requires C,63.49; H,5.17; N,19.06%.

EXAMPLE 53

4-Amino-6,7-dimethoxy-2-(4-methoxy-5,6,7,8-tetrahydro-1,3,7-triazanaphth-7-yl)-5-phenylquinazoline (a) 7-Benzyl-4-chloro-5,6,7,8-tetrahydro-1,3,7-triazanaphthalene 7-Benzyl-4-hydroxy-5,6,7,8-tetrahydro-1,3,7-triazanaphthalene [Ozdowska et al Rocz. Chem. Ann. Soc. Chim. Pol. 50, 1771 (1976)] 95.0 g, 15.9 mmol) was added to $POCl_3$ and the mixture heated to 100° C. for 1 h. The reaction was cooled, concentrated under reduced pressure and the residue quenched with ice. After neutralising with $K_2CO_3$ the product was extracted with $CH_2Cl_2$, the organic layer washed with $H_2O$, dried over $MgSO_4$ and evaporated to give the subtitle compound as a brown oil (3.33 g, 81%). $R_f$ 0.45 ($CH_2Cl_2$/MeOH/0.88$NH_3$ 92/7/1, v/v).

(b) 7-Benzyl-4-methoxy-5,6,7,8-tetrahydro-1,3,7-triazanaphthalene

Sodium (380 mg, 16.5 mmol) was added portionwise to MeOH (7 ml) and the solution was added dropwise to a solution of the product of step (a) (3.3 g, 12.7 mmol) in THF (30 ml). After stirring at room temperature for 18 h, the reaction mixture was concentrated under reduced pressure, partitioned between $H_2O$ and $CH_2Cl_2$, the aqueous layer extracted with $CH_2Cl_2$ and the combined organic layers dried over $MgSO_4$. Evaporation under reduced pressure afforded the subtitle compound as a brown oil (3.1 g, 95%). $R_f$ 0.64 ($CH_2Cl_2$/MeOH/0.88$NH_3$ 92/7/1, v/v).

(c) 4-Methoxy-5,6,7,8-tetrahydro-1,3,7-triazanaphthalene

To a solution of the product of step (b) (3.1 g, 12.0 mmol) in EtOH (40 ml) was added palladium hydroxide (20%, w/w, 614 mg) and the mixture was hydrogenated at 345 kPa [50 psi] pressure for 18 h, after which time a further portion of EtOH (40 ml) and palladium hydroxide (614 mg) was added and the hydrogenation continued for a further 18 h. Filtration, evaporation under reduced pressure and chromatography on silica gel, eluting with $CH_2Cl_2$/MeOH (90/10, v/v) afforded the subtitle compound as a pale orange oil (1.09 g, 55%). $R_f$ 0.06 ($CH_2Cl_2$/MeOH 95/5, v/v). MS m/z 166 ($MH^+$).

(d) 4-Amino-6,7-dimethoxy-2-(4-methoxy-5,6,7,8-tetrahydro-1,3,7-triazanaphth-7-yl)-5-phenylquinzoline The title compound was prepared by the method of 16(h) from the product of step (c) and the compound of Example 16(g) in the presence of 1 mol equivalent of ammonium chloride. The product was purified by chromatography on silica gel, eluting with EtOAc to afford the title compound (10%) as a foam. $R_f$ 0.42 (EtOAc/MeOH 95/5, v/v). MS m/z 445 ($MH^+$). $^1H$ NMR ($CDCl_3$) δ: 2.74 (2H, t), 3.48 (3H, s), 3.98 (3H, s), 4.00 (3H, s), 4.10 (2H, t), 4.61 (2H, bs), 4.95 (2H, s), 6.97 (1H, s), 7.38 (2H, m), 7.50 (3H, m), 8.57 (1H, s). Found: C,63.88; H,5.59; N,17.82; $C_{24}H_{24}N_6O_3$ 0.2.EtOAc 0.3.$H_2O$ requires C,63.71; H,5.65; N,17.98%.

EXAMPLE 54

4-Amino-6,7-dimethoxy-2-[6-(2-methyl-4,5,6,7-tetrahydrothiazolo-[5,4-c]pyridyl)]-5-phenylquinazoline (a) 2-Methyl-4,5,6,7-tetrahydrothiazolo-[5,4-c]pyridine hydrochloride A mixture of 3-bromo-4-piperidone hydrobromide [Scarponi et al Farmaco, Ed. Sci. 43, 575 (1988)] (2.58 g, 0.01 mol) and thioacetamide (940 mg, 0.013 mol) in EtOH (100 ml) was heated at reflux for 3 h. After cooling, the reaction mixture was cooled and evaporated under reduced pressure and the resulting residue triturated with acetone to afford a solid. This was dissolved in $H_2O$, washed with EtOAc (3×), the aqueous phase was basified with saturated aqueous $Na_2CO_3$ and extracted with EtOAc (5×), the combined organic extracts washed with saturated brine and dried over $MgSO_4$ The product was purified by chromatography on silica gel, eluting with $CH_2Cl_2$/MeOH/0.88$NH_3$ (90/10/1, v/v) followed by conversion to the hydrochloride salt with ethereal HCl to give, on filtration and drying in vacuo, the subtitle compound as a white solid (380 mg, 20%). $R_f$ 0.67 ($CH_2Cl_2$/MeOH/0.88$NH_3$ 90/1011, v/v). MS m/z 155 ($MH^+$)

(b) 4-Amino-6,7-dimethoxy-2-[6-(2-methyl-4,5,6,7-tetrahydrothiazolo-[5,4-c]pyridyl)]-5-phenylquinazoline The title compound was prepared by the method of 16(h) from the product of step (a) and the compound of Example 16(g). The product was purified by chromatography on silica gel, eluting with EtOAc, followed by trituration with ether to afford the title compound (11%) as a solid. $R_f$ 0.24 (EtOAc). MS m/z 434 ($MH^+$). $^1H$ NMR ($CDCl_3$) δ: 2.66 (3H, s) 2.90 (2H, t), 3.50 (3H, s), 3.97 (3H, s), 4.16 (2H, t), 4.61 (2H, bs), 4.97 (2H, s), 6.95 (1H, s), 7.38 (2H, m), 7.48 (3H, m).

EXAMPLE 55

The compound of Example 17 was tested in the first screen described above ("Contractile responses of human prostate") and found to have a $pA_2$ value of 8.5.

What is claimed is:

1. A compound of formula I,

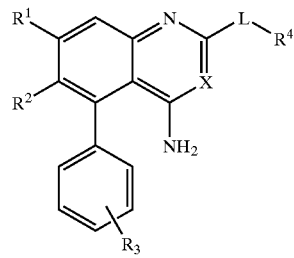

I wherein $R^1$ represents $C_{1-4}$ alkoxy optionally substituted by one or more fluorine atoms;

$R^2$ represents $C_1$ alkoxy;

$R^3$ represents one or more groups independently selected from H, halogen, $C_{1-4}$ alkoxy and $CF_3$;

wherein $R^2$ and one $R^3$ group together represent —$OCH_2$—, the methylene group being attached to the ortho-position of the pendant phenyl ring;

$R^4$ represents a group having the formula II, III, IV, V, or VI,

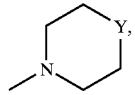

II

-continued

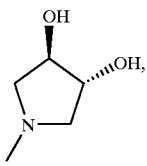

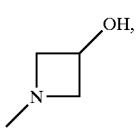

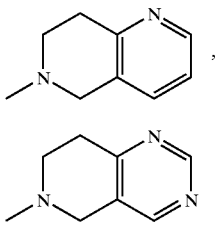

Y represents O, CH$_2$, SO$_2$, NR$^5$ or CHF; and
R$^5$ represents H or C$_{1-4}$ alkyl;

X represents N; and

L is absent;
or represents a cyclic group of formula Ia,

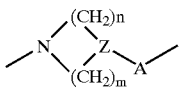

in which N is attached to the 2-position of the quinazoline ring;
A is absent or represents CO or SO$_2$;
Z represents CH or N;
m represents 1 or 2, and in addition, when Z represents CH, it may represent 0; and
n represents 1, 2 or 3, provided that the sum of m and n is 2, 3, 4 or 5;

or represents a chain of formula Ib,

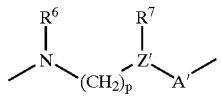

in which N is attached to the 2-position of the quinazoline ring;
A' and Z' have the same significance as A and Z above, respectively;
R$^6$ and R$^7$ independently represent H or C$_{1-4}$ alkyl; and
p represents 1, 2 or 3;
or a pharmaceutically acceptable salt thereof.

2. A compound as claimed in claim 1, wherein R$^1$ represents methoxy.

3. A compound as claimed in claim 1, wherein R$^3$ additionally represents H or 4-fluoro.

4. A compound as claimed in claim 1, wherein R$^4$ represents a group of formula II.

5. A compound as claimed in claim 4, wherein Y represents O.

6. A compound as claimed in claim 1, wherein L is absent or represents a group of formula VII,

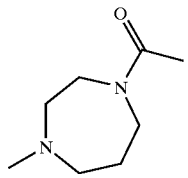

7. A pharmaceutical formulation comprising a compound of formula I, as defined in claim 1, or a pharmaceutically acceptable salt thereof, in admixture with a pharmaceutically acceptable adjuvant, diluent or carrier.

8. A method of treatment of benign prostatic hyperplasia, which comprises administration of an effective amount of a compound of formula I, as defined in claim 1, or a pharmaceutically acceptable salt thereof, to a patient in need of such treatment.

* * * * *